(12) United States Patent
Lewis et al.

(10) Patent No.: US 12,171,177 B2
(45) Date of Patent: Dec. 24, 2024

(54) GENETIC APPROACH FOR ACHIEVING ULTRA LOW NICOTINE CONTENT IN TOBACCO

(71) Applicants: North Carolina State University, Raleigh, NC (US); 22ND CENTURY LIMITED, LLC, Willamsville, NY (US)

(72) Inventors: Ramsey S. Lewis, Apex, NC (US); Ralph E. Dewey, Apex, NC (US); Juan Sanchez Tamburrino, Williamsville, NY (US)

(73) Assignees: North Carolina State University, Raleigh, NC (US); 22ND CENTURY LIMITED, LLC, Mocksville, NC (US)

( * ) Notice: Subject to any disclaimer, the term of this patent is extended or adjusted under 35 U.S.C. 154(b) by 192 days.

(21) Appl. No.: 17/785,153

(22) PCT Filed: Jan. 8, 2021

(86) PCT No.: PCT/US2021/012742
§ 371 (c)(1),
(2) Date: Jun. 14, 2022

(87) PCT Pub. No.: WO2021/142296
PCT Pub. Date: Jul. 15, 2021

(65) Prior Publication Data
US 2023/0029171 A1 Jan. 26, 2023

Related U.S. Application Data

(60) Provisional application No. 62/958,505, filed on Jan. 8, 2020.

(51) Int. Cl.
| | | |
|---|---|---|
| A24B 3/12 | (2006.01) | |
| A01C 21/00 | (2006.01) | |
| A01G 22/45 | (2018.01) | |
| A01H 1/00 | (2006.01) | |
| A01H 6/82 | (2018.01) | |
| A24B 15/10 | (2006.01) | |
| C12N 15/82 | (2006.01) | |
| A01C 23/04 | (2006.01) | |

(52) U.S. Cl.
CPC ............ *A01H 1/101* (2021.01); *A01C 21/00* (2013.01); *A01G 22/45* (2018.02); *A01H 6/823* (2018.05); *A24B 3/12* (2013.01); *A24B 15/10* (2013.01); *A01C 23/042* (2013.01)

(58) Field of Classification Search
None
See application file for complete search history.

(56) References Cited

U.S. PATENT DOCUMENTS

| | | | |
|---|---|---|---|
| 5,125,420 A | 6/1992 | Livingston | |
| 2012/0234334 A1* | 9/2012 | Chen | A24B 15/22 131/306 |
| 2016/0374387 A1* | 12/2016 | Adams | C12N 15/8218 131/336 |
| 2018/0346917 A1* | 12/2018 | Dewey | C12N 15/52 |

FOREIGN PATENT DOCUMENTS

| | | |
|---|---|---|
| CN | 109644808 B | 4/2019 |
| WO | 2018119124 A1 | 6/2018 |
| WO | 2019140312 A1 | 7/2019 |
| WO | 2019185703 A1 | 10/2019 |
| WO | 2019212632 A1 | 11/2019 |
| WO | 2021247740 A1 | 12/2021 |

OTHER PUBLICATIONS

International Search Report and Written Opinion of the International Searching Authority corresponding to International Application No. PCT/US2021/012742, mailed Apr. 2, 2021 (14 pages).
Caldwell, Eric F., "A study of Irrigation, Fertigation and Plasticulture in Burley Tobacco, with a Focus on Yield, Quality and TSNA Reduction", Master's Thesis, University of Tennessee, 2008. Retrieved from https://trace.tennessee.edu/utk_gradthes/340.
Lewis, Ramsey, "Tobacco Breeding Projects at N.C. State University", Presention of Oct. 19, 2018.
Extended European Search Report corresponding to EP 21738001.3; dated Dec. 7, 2023 (10 pages).
Lewis, Ramsey S., et al., "Genetic and Agronomic Analysis of Tobacco Genotypes Exhibiting Reduced Nicotine Accumulation Due to Induced Mutations in Berberine Bridge Like ( BBL) Genes", Frontiers in Plant Science. 11:368, 2020.
Lewis, Ramsey S., et al., "Transgenic and Mutation-Based Suppression of a Berberine Bridge Enzyme-Like (BBL) Gene Family Reduces Alkaloid Content in Field-Grown Tobacco", PLoS One. 10(2): e0117273, 2015.
Lopez, Harry O., "Developing Non-GMO Tobacco Cultivars with Lower Alkaloid Content Using a Reverse Genetics Strategy", M. Sc. Thesis of Harry O. Lopez submitted to Graduate Faculty of NCSU, 2011.

* cited by examiner

*Primary Examiner* — Weihua Fan
(74) *Attorney, Agent, or Firm* — Myers Bigel, P.A.

(57) ABSTRACT

The present invention relates to tobacco products from plants comprising mutated berberine bridge enzyme-like nucleic acids and the recessive nic1 and/or nic2 alleles and methods of making the same.

9 Claims, 2 Drawing Sheets

GENETIC APPROACH FOR ACHIEVING ULTRA LOW NICOTINE CONTENT IN TOBACCO

CROSS-REFERENCE TO RELATED APPLICATIONS

The present application claims the benefit of priority to U.S. Application No. 62/958,505, filed on Jan. 8, 2020, the contents of which are incorporated herein in their entirety.

FIELD OF THE INVENTION

The present invention relates to tobacco products from plants comprising mutated berberine bridge enzyme-like nucleic acids and the recessive nic1 and/or nic2 alleles and methods of making the same.

BACKGROUND OF THE INVENTION

The pyridine alkaloids of tobacco (*Nicotiana tabacum* L.) are among the most studied group of plant secondary compounds. Nicotine constitutes greater than 90% of the total alkaloid pool in most tobacco genotypes and is primarily responsible for the pharmacological response experienced by users of tobacco products. In decreasing order of relative abundance, the remaining major alkaloids in tobacco include anatabine, nornicotine, and anabasine. Alkaloid levels in tobacco are influenced by environmental conditions, interactions with plant pests, and plant genetics.

Although nicotine is the primary compound that gives the users of tobacco products the pharmacological effect they seek, there are several circumstances where it would be desirable to develop products using tobacco plants that produce and accumulate very low levels of nicotine. For example, some studies have shown that the use of low-nicotine cigarettes as a component in smoking cessation strategies can help smokers who are trying to quit (Hatsukami et al., 2010a; Donny et al., 2014). Other reports have demonstrated that by lowering the nicotine levels below a critical threshold in tobacco products, they can no longer initiate or maintain an addiction response (Benowitz and Henningfield, 1994; Benowitz et al., 2007). Studies such as these may ultimately influence regulatory agencies, such as the U.S. Food and Drug Administration, who have been given the authority to determine what acceptable levels of various tobacco constituents (including nicotine) will be allowable in cigarettes and other tobacco products.

SUMMARY OF THE INVENTION

In one aspect, the disclosure of the present technology provides a method of curing one or more leaves of a *Nicotiana* plant comprising: (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2, the method comprising: (a) a yellowing process comprising heating the leaf at a temperature starting at 92° F.-96° F. and increasing to a temperature of 104° F.-108° F. at a rate of about 1° F. per hour until reaching a maximum upper temperature and holding at the upper temperature for a period of about 52-58 hours; (b) a leaf drying process comprising drying at a temperature of about 120° F. for about 22 hours; and (c) a stem drying process comprising drying at a temperature of about 132° F.-138° F. for about 50 hours to about 65 hours, thereby curing the one or more leaves of the *Nicotiana* plant and producing one or more cured leaves of the *Nicotiana* plant.

In some embodiments, the *Nicotiana* plant comprises (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 and a recessive allele of nic2. In some embodiments, the recessive allele of nic1 is a homozygous recessive allele. In some embodiments, the recessive allele of nic2 is a homozygous recessive allele. In some embodiments, the *Nicotiana* plant has a nicotinic alkaloid content that is reduced as compared to a plant that is modified per (A) only (e.g., not modified per (A) and (B)).

In some embodiments, the present technology provides a cured leaf of the *Nicotiana* plant produced by the method, wherein the cured leaf comprises (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2. In some embodiments, the cured leaf comprises (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 and a recessive allele of nic2. In some embodiments, the recessive allele of nic1 is a homozygous recessive allele. In some embodiments, the recessive allele of nic2 is a homozygous recessive allele. In some embodiments, the leaf comprises a reduced nicotinic alkaloid content as compared to a leaf of a wild-type control *Nicotiana* plant or as compared to a Nic1/Nic2 control *Nicotiana* plant. In some embodiments, the nicotinic alkaloid is nicotine. In some embodiments, the cured leaf comprises a nicotine content of 0.5 mg/g or less. In some embodiments, the cured leaf comprises a nicotine content of 0.4 mg/g or less. In some embodiments, the leaf comprises increased levels of sugar and/or reduced levels of ammonia as compared to a leaf that was cured according to standard curing methods. In some embodiments, the *Nicotiana* plant further comprises reduced expression of a polynucleotide encoding an additional nicotinic alkaloid biosynthetic enzyme selected from the group consisting of aspartate oxidase, quinolinate synthase, quinolate phosphoribosyl transferase, ornithine decarboxylase, putrescine N-methyltransferase, methyl putrescine oxidase, and A622.

In some embodiments, the present technology provides a tobacco product comprising the cured leaf. In some embodiments, the tobacco is selected from the group consisting of leaf tobacco, shredded tobacco, cut tobacco, ground tobacco, powder tobacco, tobacco extract, smokeless tobacco, moist or dry snuff, pipe tobacco, cigar tobacco, cigarillo tobacco, cigarette tobacco, and chewing tobacco. In some embodiments, the product is selected from the group consisting of a cigarillo, a kretek cigarette, a non-ventilated recess filter cigarette, a vented recess filter cigarette, a cigar, snuff, a tobacco-containing gum, a tobacco-containing lozenge, and a chewing tobacco.

In some embodiments, the disclosure of the present technology provides a method of improving the yield of the *Nicotiana* plant, the method comprising: (a) fertilizing seedlings at a stage of about 90% germination, the fertilizing is carried out through fertigation, optionally the concentration of N in the fertilizer is about 200 ppm; (b) applying a plastic mulch treatment; and (c) applying to the seedlings nitrogen at a rate of about 90-120 lbs/acre N total at about 4 to 5 weeks after transplanting, at about 6 to 7 weeks after transplanting, and at about 8 to 9 weeks after transplanting to provide increased yield and quality of the *Nicotiana* plant. In some embodiments, the nitrogen is applied using fertigation. In some embodiments, the substrate is covered with a ground cover sheeting, thereby providing a substrate covered with ground cover sheeting. In some embodiments, the substrate and/or the substrate covered with ground cover sheeting is covered with mulch.

In one aspect, the disclosure of the present technology provides a cured tobacco leaf from a *Nicotiana* plant, wherein the *Nicotiana* plant (1) comprises one or both of the recessive nic1 and nic2 alleles and (2) comprises BBLa, BBLb, and BBLc genes that are altered, relative to wild type, so as to reduce the activity of BBLa, BBLb, and BBLc or to reduce the expression of a nucleic acid encoding BBLa, a nucleic acid encoding BBLb, and a nucleic acid encoding BBLc, such that the nicotinic alkaloid content of the *Nicotiana* plant is reduced as compared to a control *Nicotiana* plant. In some embodiments, the *Nicotiana* plant comprises both of the recessive nic1 and nic2 alleles. In some embodiments, the recessive allele of nic1 is a homozygous recessive allele. In some embodiments, the recessive allele of nic2 is a homozygous recessive allele. In some embodiments, the cured leaf comprises a USDA Grade Index that is comparable to or improved as compared to the USDA Grade Index of a cured leaf from a control *Nicotiana* plant. In some embodiments, the leaf comprises a USDA Grade Index of about 60 or higher. In some embodiments, the yield of cured leaf is comparable to or increased as compared to a control *Nicotiana* plant. In some embodiments, the nicotinic alkaloid is nicotine.

In some embodiments, the present technology provides a tobacco product comprising the cured leaf. In some embodiments, the tobacco is selected from the group consisting of leaf tobacco, shredded tobacco, cut tobacco, ground tobacco, powder tobacco, tobacco extract, smokeless tobacco, moist or dry snuff, pipe tobacco, cigar tobacco, cigarillo tobacco, cigarette tobacco, and chewing tobacco. In some embodiments, the tobacco product is selected from the group consisting of a cigarillo, a kretek cigarette, a non-ventilated recess filter cigarette, a vented recess filter cigarette, a cigar, snuff, a tobacco-containing gum, a tobacco-containing lozenge, and a chewing tobacco.

In one aspect, the disclosure of the present technology provides a method of producing a *Nicotiana* plant having reduced nicotinic alkaloid content, comprising combining in a *Nicotiana* plant: (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2, wherein the *Nicotiana* plant has a nicotinic alkaloid content that is reduced as compared to a plant that is modified per (A) only (e.g., not modified per (A) and (B)). In some embodiments, the *Nicotiana* plant comprises the recessive allele of nic1. In some embodiments, the *Nicotiana* plant comprises the recessive allele of nic1 and the recessive allele of nic2. In some embodiments, the recessive allele of nic1 is a homozygous recessive allele. In some embodiments, the recessive allele of nic2 is a homozygous recessive allele. In some embodiments, the method further comprises reducing expression of a polynucleotide encoding an additional nicotinic alkaloid biosynthetic enzyme selected from the group consisting of aspartate oxidase, quinolinate synthase, quinolate phosphoribosyl transferase, ornithine decarboxylase, putrescine N-methyltransferase, methyl putrescine oxidase, and A622.

In some embodiments, the *Nicotiana* plant has a nicotinic alkaloid content that is reduced by at least 40% as compared to a plant that is modified per (A) only (e.g., not modified per (A) and (B)). In some embodiments, the nicotinic alkaloid is nicotine and the nicotine content is reduced by about 40% to about 90% as compared to a plant that is modified per (A) only (e.g., not modified per (A) and (B)). In some embodiments, the nicotinic alkaloid is nicotine and the nicotine content is about 0.014% to about 0.098%. In some embodiments, the plant comprises (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2. In some embodiments, the recessive allele of nic1 is a homozygous recessive allele. In some embodiments, the recessive allele of nic2 is a homozygous recessive allele.

In some embodiments, the present technology provides a progeny plant or seed produced from the plant, wherein the progeny plant or seed comprises (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2. In some embodiments, the recessive allele of nic1 is a homozygous recessive allele. In some embodiments, the recessive allele of nic2 is a homozygous recessive allele.

In one aspect, the disclosure of the present technology provides a tobacco product comprising tobacco from a *Nicotiana* plant, wherein the *Nicotiana* plant comprises: (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2, wherein the *Nicotiana* plant has a nicotinic alkaloid content that is reduced as compared to a plant that is modified per (A) only (e.g., not modified per (A) and (B)). In some embodiments, the recessive allele of nic1 is a homozygous recessive allele. In some embodiments, the recessive allele of nic2 is a homozygous recessive allele. In some embodiments, the *Nicotiana* plant is modified so as to reduce the activity of BBLa, BBLb, and BBLc and/or expression of a nucleic acid encoding BBLa, BBLb, and BBLc, and comprises the recessive allele of nic1. In some embodiments, the *Nicotiana* plant is modified so as to reduce the activity of BBLa, BBLb, and BBLc and/or expression of a nucleic acid encoding BBLa, BBLb, and BBLc, and comprises the recessive allele of nic1 and the recessive allele of nic2. In some embodiments, the *Nicotiana* plant has a nicotinic alkaloid content that is reduced by at least 40% as compared to a plant that is modified per (A) only. In some embodiments, the nicotinic alkaloid is nicotine and the nicotine content is reduced by about 40% to about 90% as compared to a plant that is modified per (A) only. In some embodiments, the nicotinic alkaloid is nicotine and the nicotine content is about 0.014% to about 0.098%. In some embodiments, the nicotinic alkaloid is nicotine and the nicotine content is about 0.014%. In some embodiments, the tobacco is selected from the group consisting of leaf tobacco, shredded tobacco, cut tobacco, ground tobacco, powder tobacco, tobacco extract, smokeless tobacco, moist or dry snuff, pipe tobacco, cigar tobacco, cigarillo tobacco, cigarette tobacco, and chewing tobacco. In some embodiments, the product is selected from the group consisting of a cigarillo, a kretek cigarette, a non-ventilated recess filter cigarette, a vented recess filter cigarette, a cigar, snuff, a tobacco-containing gum, a tobacco-containing lozenge, and a chewing tobacco. In some embodiments, the *Nicotiana* plant further comprises reduced expression of a polynucleotide encoding an additional nicotinic alkaloid biosynthetic enzyme selected from the group consisting of aspartate oxidase, quinolinate synthase, quinolate phosphoribosyl transferase, ornithine decarboxylase, putrescine N-methyltransferase, methyl putrescine oxidase, and A622.

In one aspect, the present invention provides a cured tobacco leaf from a *Nicotiana* plant, wherein (A) the *Nicotiana* plant (1) comprises one or both of the recessive nic1 and nic2 alleles and (2) comprises BBLa, BBLb, and BBLc genes that are altered, relative to wild type, such that the nicotinic alkaloid content of the *Nicotiana* plant is reduced compared to said wild type (e.g., no BBLabc, no nic1 and no nic2); and (B) the cured tobacco leaf has the characteristics of a fair to good quality leaf with good color intensity, normal width and uniform texture, optionally wherein the cured tobacco leaf has a USDA grade index of over 60 or is of a good to fair to low quality or fine to good to fair quality per the USDA Standard Grades ("Official Standard Grades for Flue-Cured Tobacco U.S. Types 11, 12, 13, 14, and Foreign Type 92").

In one aspect, a method of producing a *Nicotiana* plant having reduced nicotinic alkaloid content is provided, the method comprising combining in a *Nicotiana* plant: (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2, wherein the *Nicotiana* plant has a nicotinic alkaloid content that is reduced as compared to a plant that is modified per (A) only.

In one aspect, a method of curing one or more leaves of a *Nicotiana* plant comprising: (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2, wherein the *Nicotiana* plant has a nicotinic alkaloid content that is reduced as compared to a plant that is modified per (A) only, the method comprising: (a) a yellowing process comprising heating the leaf at a temperature starting at 92° F.-96° F. and increasing to a temperature of 104° F.-108° F. at a rate of about 1° F. per hour until reach maximum upper temperature and hold at the upper temperature for a period of about 52-58 hours; (b) a leaf drying process at a temperature of about 120° F. for about 22 hours; and (c) a stem drying process at a temperature of about 132° F.-138° F. for about 50 hours to about 65 hours with continuous monitoring, thereby curing the one or more leaves of the *Nicotiana* plant and producing one or more cured leaves of the *Nicotiana* plant. In some embodiments, the leaf drying process occurs at a temperature of about 116° F.-120° F. for about 28-34 hours. In some embodiments, the leaf drying process occurs at a temperature of about 116° F.-118° F. for about 28-34 hours. In some embodiments, the disclosure of the present technology relates to a cured leaf of a *Nicotiana* plant produced by the method of curing. In some embodiments, the leaf is an ultra-low nicotine leaf comprising 0.04% nicotine or less. In some embodiments, the leaf comprises increased levels of sugar and/or ammonia as compared to a leaf that was cured according to standard curing methods. In some embodiments, the *Nicotiana* plant further comprises reduced expression of a polynucleotide encoding an additional nicotinic alkaloid biosynthetic enzyme selected from the group consisting of aspartate oxidase, quinolinate synthase, quinolate phosphoribosyl transferase, ornithine decarboxylase, putrescine N-methyltransferase, methyl putrescine oxidase, and A622. In some embodiments, the disclosure of the present technology relates to a tobacco product comprising the cured leaf produced by the curing methods described herein. In some embodiments of the tobacco product, the tobacco is selected from the group consisting of leaf tobacco, shredded tobacco, cut tobacco, ground tobacco, powder tobacco, tobacco extract, smokeless tobacco, moist or dry snuff, pipe tobacco, cigar tobacco, cigarillo tobacco, cigarette tobacco, and chewing tobacco. In some embodiments, the tobacco product is selected from the group consisting of a cigarillo, a kretek cigarette, a non-ventilated recess filter cigarette, a vented recess filter cigarette, a cigar, snuff, a tobacco-containing gum, a tobacco-containing lozenge, and a chewing tobacco.

In one aspect, a method of improving the yield and quality of a *Nicotiana* plant of the invention is provided, the method comprising: (a) fertilizing seedlings at a stage of about 90% germination, the fertilizing is carried out through fertigation (e.g., drip irrigation), optionally the concentration of N is about 200 ppm; (b) applying a plastic mulch treatment; e.g., a plastic mulch is added to cover the fertigation equipment (e.g., drip tape/tube); and (c) applying nitrogen at a rate of about 90-120 lbs/acre N total, to the seedlings at about 4 to 5 weeks after transplanting, at about 6 to 7 weeks after transplanting, and at about 8 to 9 weeks after transplanting, to provide increased yield and quality of the *Nicotiana* plant.

In one aspect, a tobacco product is provided, the tobacco product comprising tobacco from a *Nicotiana* plant, wherein the *Nicotiana* plant comprises: (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2, wherein the *Nicotiana* plant has a nicotinic alkaloid content that is reduced as compared to a plant that is modified per (A) only.

The present invention further provides plants and plant parts thereof produced by the methods of the invention as well as crops, progeny, and products produced from said plants and parts thereof, and seeds from the plants. The invention further provides vectors and expression cassettes for carrying out the methods of the invention.

These and other aspects of the invention are set forth in more detail in the description of the invention below.

DETAILED DESCRIPTION OF THE INVENTION

Figure 1:
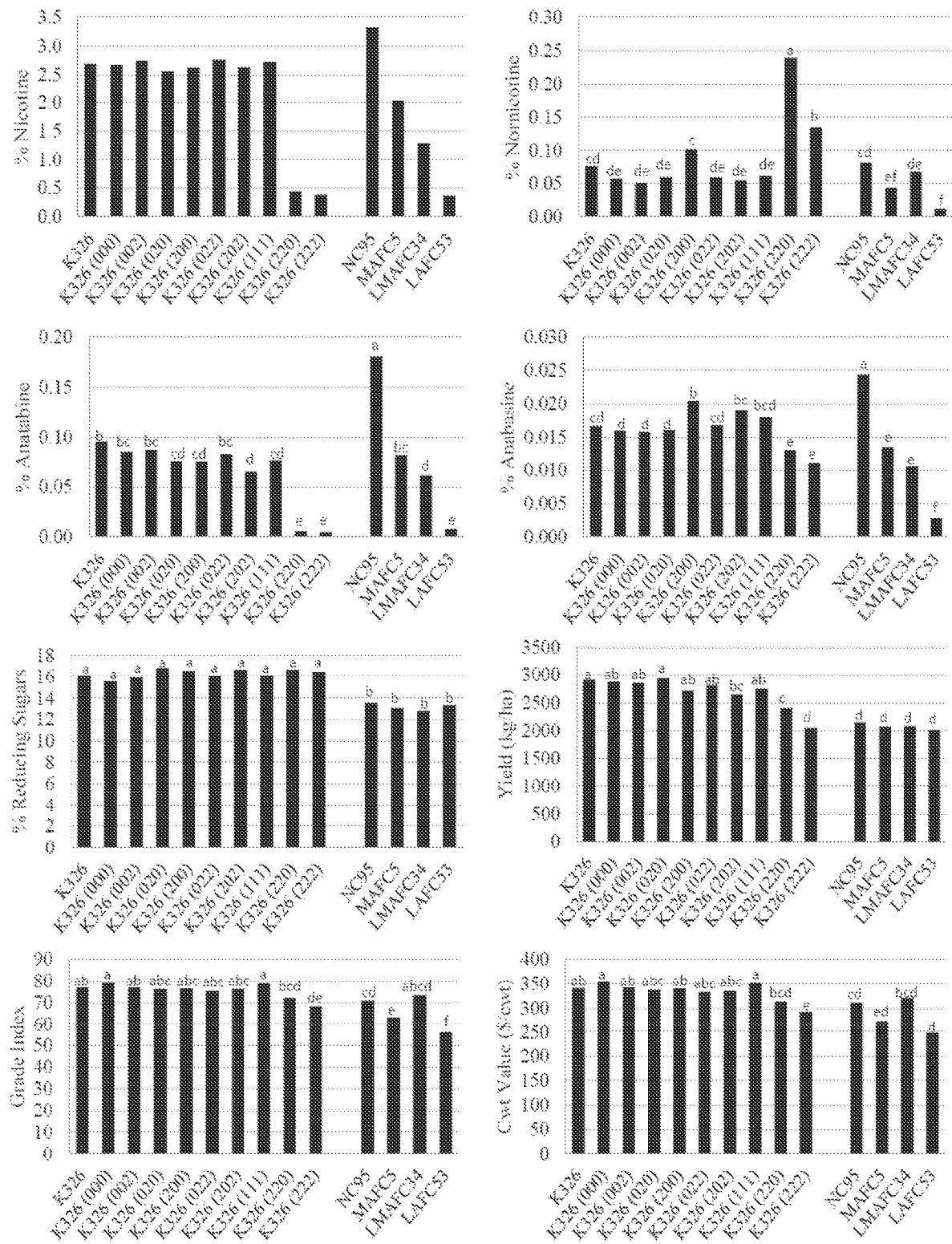
FIG. 1 shows entry means for flue-cured genetic materials evaluated for alkaloid levels, yield, and quality determinations. Means are averaged over six 2016 and 2017 North Carolina field environments. Means with different letters are significantly different from each other at the P<0.05 level of significance.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 15%, 25%, 50%, 75%, 100%, 150%, 200%, 300%, 400%, 500% or more as compared to a control.

As used herein, the terms "reduce," "reduced," "reducing," "reduction," "diminish," "suppress," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In some embodiments, the reduction can result in no or essentially no (i.e., an insignificant amount, e.g., less than about 10% or even 5%) detectable activity or amount. Thus, for example, reduced transcription of one or more target DNA can mean a reduction in the transcription of the target gene of at least about 30%, 35%, 40%, 45%, 50%, 55%, 60%, 65%, 70%, 75%, 80%, 85%, 90%, 95%, 96%, 97%, 98%, 99%, or 100% as compared to a control (e.g., a plant not comprising the mutation in the BBLa, BBLb, and BBLc nucleic acids).

As used herein, the term "very low nicotine" or "VLN" tobacco refers to tobacco comprising 0.5 mg nicotine/gram tobacco or less.

As used herein, the terms "standard curing methods," "standard methods of curing," "standard curing protocol," or "standard tobacco curing methods," and the like refer to a known tobacco curing method (such as, e.g., methods described in Powell 1987 (Manual entitled Powell Manufacturing, Co.'s Bulk Curing/Drying Owner's Operator's Manual for Flue Cured Tobaccos, Powell Manufacturing, Co. (Jan. 20, 1987)).

As used herein, "chimeric" refers to a nucleic acid molecule or a polypeptide in which at least two components are derived from different sources (e.g., different organisms, different coding regions).

"Complement" as used herein can mean 100% complementarity or identity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express, for example, a polypeptide of interest or a functional untranslated RNA.

A "fragment" or "portion" of a nucleotide sequence will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or substantially identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent.

As used herein, the term "gene" refers to a nucleic acid molecule capable of being used to produce mRNA, antisense RNA, RNAi (miRNA, siRNA, shRNA), anti-microRNA antisense oligodeoxyribonucleotide (AMO), and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

A "heterologous" or a "recombinant" nucleic acid is a nucleotide sequence not naturally associated with a host cell into which it is introduced, including non-naturally occurring multiple copies of a naturally occurring nucleotide sequence. Alternatively, a heterologous nucleotide sequence can be one that does not naturally occur with another nucleotide sequence to which it is associated. For example, a nucleic acid construct comprising a "heterologous promoter" operably associated with a nucleic acid molecule is a promoter that does not naturally occur with said nucleic acid molecule to which it is associated.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention.

As used herein, hybridization, hybridize, hybridizing, and grammatical variations thereof, refer to the binding of two fully complementary nucleotide sequences or substantially complementary sequences in which some mismatched base pairs may be present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, NY).

As used herein, "modify," "modifying" or "modification" (and grammatical variations thereof) of a means any alteration of a BBL polynucleotide (e.g., BBLa, BBLb, BBLc) and/or BBL polypeptide or other polypeptide or polynucleotide that results in the reduction or elimination of the expression of the nucleic acids and/or the production and/or activity of the polypeptides. Such modifications can include, but are not limited to, deleting or inserting one or more nucleotides or an entire nucleic acid region (transcribed and untranscribed regions), and/or introducing one or more point mutations, which reduce or eliminate the expression of the nucleic acids and/or the production and/or activity of the polypeptides.

As used herein, the terms "modulate," "modulates," "modulated" or "modulation" refer to enhancement (e.g., an increase) or inhibition (e.g., a reduction) in a specified activity (e.g., modulated nicotine production/content). Thus, in some embodiments, an elevation or increase in activity (e.g., nuclease activity) of about 15%, 25%, 50%, 75%, 100%, 150%, 200%, 300%, 400%, 500% or more as compared to a control may be observed. In other embodiments, a reduction in expression level or activity (e.g., BBLa, BBLb, and BBLc expression level or BBLa, BBLb, and BBLc polypeptide activity) of about 30%, 35%, 40%, 45%, 50%, 55%, 60%, 65%, 70%, 75%, 80%, 85%, 90%, 95%, 96%, 97%, 98%, 99%, or 100% may be observed as compared to a control.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type nucleic acid" is a nucleic acid that is naturally occurring in or endogenous to the organism. A "homologous" nucleic acid sequence is a nucleotide sequence naturally associated with a host cell into which it is introduced. A "wild type" strain or line of tobacco, as used herein, refers to a tobacco strain or line that does not comprise the BBLabc mutations or the recessive nic1 and/or nic2 alleles. A "Nic1/Nic2 control" strain or line of tobacco, as used herein, refers to a tobacco strain or line that does not comprise the homozygous recessive nic1 and/or nic2 alleles.

In some embodiments, as described herein, the plants of the present technology comprise BBLabc mutations that are homozygous for the three major bbl mutations (e.g., bbl-a/bbl-a, bbl-b/bbl-b, bbl-c/bbl-c), and also homozygous for the recessive nic1 and/or nic2 alleles (e.g., nic1/nic1, nic2/nic2).

Also as used herein, the terms "nucleic acid," "nucleic acid molecule," "nucleic acid construct," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The nucleic acid constructs of the present disclosure can be DNA or RNA, but are preferably DNA. Thus, although the nucleic acid constructs of this invention may be described and used in the form of DNA, depending on the intended use, they may also be described and used in the form of RNA.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. All nucleic acids provided herein have 5' and 3' ends. Further, except as otherwise indicated, nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, a "target DNA," "target region" or a "target region in the genome" refers to a region of an organism's genome that is fully complementary or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a region of a gene against which any class of custom designed nuclease (e.g., ZFN, TALEN, meganuclease, CRISPR-Cas and the like) has been engineered to bind and cleave.

As used herein, the phrase "substantially identical," or "substantial identity" in the context of at least two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue sequence identity, when compared and aligned for maximum correspondence, as measured using one of the following sequence comparison algorithms or by visual inspection.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

A nucleotide sequence of interest (e.g., nucleic acids encoding nucleases useful for mutating BBL nucleic acids) can be operably associated with a variety of promoters, terminators, and/or other regulatory elements for expression in plant cell. Any promoter, terminator or other regulatory element functional in a plant cell may be used with the nucleic acids of this invention. In some embodiments, a promoter may be operably linked to a polynucleotide and/or nucleic acid useful in carrying out the invention. In some embodiments, a terminator may be operably linked to a polynucleotide and/or nucleic acid of the invention.

A "promoter" is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II or RNA polymerase III and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." These various types of promoters are known in the art. The choice of promoter will vary depending on the temporal and spatial requirements for expression, and also depending on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate. In some embodiments, expression of a nucleotide sequence of interest can be in any plant and/or plant part, (e.g., in leaves, in stalks or stems, in ears, in inflorescences, in roots, seeds and/or seedlings, and the like) and the promoter is selected accordingly.

In some embodiments, one or more of the polynucleotides and nucleic acids of the invention may be operably associated with a promoter as well as a terminator, and/or other regulatory elements for expression in plant cell. Any promoter, terminator or other regulatory element that is functional in a plant cell may be used with the nucleic acids of this invention. Non-limiting examples of promoters useful with this invention include an *Arabidopsis thaliana* U6 RNA polymerase III promoter, a 35S promoter, actin promoter, ubiquitin promoter, Rubisco small subunit promoter, an inducible promoter, including but not limited to, a an AlcR/AlcA (ethanol inducible) promoter, a glucocorticoid receptor (GR) fusion, GVG, a pOp/LhGR (dexamethasone inducible) promoter, a XVE/OlexA (β-estradiol inducible) promoter, a heat shock promoter and/or a bidirectional promoter (See, e.g., Gatz, Christine. *Current Opinion in Biotechnology* 7(2):168-172 (1996); Borghi L. Methods Mol Biol. 655:65-75(2010); Baron et al. *Nucleic acids research* 23(17) (1995), 3605; Kumar et al. *Plant molecular biology* 87(4-5):341-353 (2015)).

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

In some embodiments, components for modifying or mutating a BBL nucleic acid and any other polynucleotide of interest (e.g., other polynucleotides encoding nicotinic alkaloid biosynthetic enzymes transcription factors that positively regulate nicotinic alkaloid biosynthesis) may be comprised in an "expression cassette." As used herein, "expression cassette" means a nucleic acid construct comprising a nucleotide sequence of interest (e.g., a nuclease useful for mutating a BBL nucleic acid), wherein said nucleotide sequence is operatively associated with at least a control sequence (e.g., a promoter). An expression cassette may be chimeric, meaning that at least one of its components is heterologous with respect to at least one of its other components. Thus, for example, the nucleic acids to be expressed may be operably linked to a promoter or other regulatory element that is heterologous to the nucleic acids to be expressed (e.g., heterologous to a CRISPR guide DNA). An expression cassette may also be one that is naturally occurring but has been obtained in a recombinant form useful for heterologous expression.

In addition to promoters, an expression cassette also can optionally include additional regulatory elements functional in a plant cell including, but not limited to, a transcriptional and/or translational termination region (i.e., termination region). A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, to the nucleotide sequence of interest, to the host, or any combination thereof). Non-limiting examples of terminators functional in a plant and useful with this invention include an actin terminator; a Rubisco small subunit terminator, a Rubisco large subunit terminator, a nopaline synthase terminator, and/or a ubiquitin terminator.

A number of non-translated leader sequences derived from viruses are known to enhance gene expression. Specifically, leader sequences from Tobacco Mosaic Virus (TMV, the "ω-sequence"), Maize Chlorotic Mottle Virus (MCMV) and Alfalfa Mosaic Virus (AMV) have been shown to be effective in enhancing expression (Gallie et al. (1987) *Nucleic Acids Res.* 15:8693-8711; and Skuzeski et al. (1990) *Plant Mol. Biol.* 15:65-79). Other leader sequences known in the art include, but are not limited to, picornavirus leaders such as an encephalomyocarditis (EMCV) 5' non-coding region leader (Elroy-Stein et al. (1989) *Proc. Natl. Acad. Sci. USA* 86:6126-6130); potyvirus leaders such as a Tobacco Etch Virus (TEV) leader (Allison et al. (1986) *Virology* 154:9-20); Maize Dwarf Mosaic Virus (MDMV) leader (Allison et al. (1986), supra); human immunoglobulin heavy-chain binding protein (BiP) leader (Macejak & Samow (1991) *Nature* 353:90-94); untranslated leader from the coat protein mRNA of AMV (AMV RNA 4; Jobling & Gehrke (1987) *Nature* 325:622-625); tobacco mosaic TMV leader (Gallie et al. (1989) *Molecular Biology of RRNA* 237-256); and MCMV leader (Lommel et al. (1991) *Virology* 81:382-385). See also, Della-Cioppa et al. (1987) *Plant Physiol.* 84:965-968.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette also can include a nucleotide sequence for a selectable marker, which can be used to select a transformed host cell. As used herein, "selectable marker" means a nucleotide sequence that when expressed imparts a distinct phenotype to the host cell expressing the marker and thus allows such transformed cells to be distinguished from those that do not have the marker. Such a nucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acids described herein can be used in connection with vectors. The term "vector" refers to a composition for transferring, delivering or introducing one or more nucleic acids into a cell. A vector comprises a nucleic acid molecule comprising the nucleotide sequence(s) to be transferred, delivered or introduced. Vectors for use in transformation of host organisms are well known in the art. Non-limiting examples of general classes of vectors include but are not limited to a viral vector, a plasmid vector, a phage vector, a phagemid vector, a cosmid vector, a fosmid vector, a bacteriophage, an artificial chromosome, or an *Agrobacterium* binary vector in double or single stranded linear or circular form which may or may not be self transmissible or mobilizable. A vector as defined herein can transform a eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms. In some representative embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell. Accordingly, the polynucleotides and/or expression cassettes can be comprised in vectors as described herein and as known in the art.

As used herein, "nicotinic alkaloid" refers to alkaloids derived from nicotinic acid. These alkaloids generally contain a 3-pyridyl ring structure, with nicotine, nornicotine, anatabine and anabasine representing the predominant nicotinic alkaloids within the genus *Nicotiana*. In some embodiments, a nicotinic alkaloid may comprise, consist essentially of, or consist of nicotine, nornicotine, anatabine and/or anabasine. In some embodiments, the nicotinic alkaloid is nicotine.

As used herein, "alkaloid content" means the total amount of alkaloids found in a plant, for example, in terms of percent dry weight (% dry weight) or percent fresh weight (% fresh weight).

A plant useful with this invention can be any *Nicotiana* plant that produces nicotine and/or other related alkaloids. Thus, in some embodiments, the plant can be *Nicotiana tabacum, Nicotiana rustica* or *Nicotiana benthamiana*. Any variety of tobacco is useful with this invention including, but not limited to, Aromatic Fire-cured, Brightleaf tobacco, Burley; Cavendish; Corojo; Criollo; Oriental Tobacco; Perique; Shade tobacco; Thuoc lao; Type 22; NC95, K326, K346, White Burley, Wild Tobacco, Y1, and the like.

The term "plant part," as used herein, includes but is not limited to reproductive tissues (e.g., petals, sepals, stamens, pistils, receptacles, anthers, pollen, flowers, fruits, flower bud, ovules, seeds, embryos); vegetative tissues (e.g., petioles, stems, roots, root hairs, root tips, pith, coleoptiles, stalks, shoots, branches, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell.

"Plant cell culture" means cultures of plant units such as, for example, protoplasts, cell culture cells, cells in plant tissues, pollen, pollen tubes, ovules, embryo sacs, zygotes and embryos at various stages of development. In some embodiments of the invention, a transgenic tissue culture or transgenic plant cell culture is provided, wherein the transgenic tissue or cell culture comprises a nucleic acid molecule/nucleotide sequence of the invention.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

"Introducing," "introduce," "introduced" (and grammatical variations thereof) in the context of a polynucleotide of interest (e.g., a nuclease useful for mutating a BBL nucleic acid) means presenting the polynucleotide of interest to the host organism or cell of said organism (e.g., host cell) in such a manner that the polynucleotide gains access to the interior of a cell. Where more than one polynucleotide is to be introduced these polynucleotides can be assembled as part of a single polynucleotide or nucleic acid construct, or as separate polynucleotides or nucleic acid constructs, and can be located on the same or different expression constructs or transformation vectors. Accordingly, these polynucleotides can be introduced into cells in a single transformation event, in separate transformation/transfection events, or, for example, they can be incorporated into an organism by conventional breeding protocols. Thus, in some aspects, one or more polynucleotides encoding nucleases useful for modifying or mutating a BBL nucleic acid (e.g., Crispr-Cas nucleases, meganucleases, zinc finger nucleases (ZFNs), and/or transcription activator-like effector nucleases (TALENs)) can be introduced singly or in combination in a single expression cassette and/or vector into a host organism or a cell of said host organism. In some embodiments, introducing a recessive allele of nic1, or a recessive allele nic1 and a recessive allele of nic2 can comprise incorporating one or more of the recessive alleles via conventional breeding into, for example, a plant comprising a modification in BBLa, BBLb, and BBLc such that the BBLa, BBLb, and BBLc genes have reduced or no expression or that the polypeptides encoded by the modified BBLa, BBLb, and BBLc genes have reduced or no activity.

The term "transformation" or "transfection" as used herein refers to the introduction of a heterologous nucleic acid into a cell, such as a nucleic acid encoding a nuclease. Transformation of a cell may be stable or transient or may be in part stably transformed and in part transiently transformed. Thus, in some embodiments, the modifications to the plant genome can be stable, and in some embodiments, the modifications can be transient. In some embodiments, after stable transformation, the nucleic acid constructs introduced to the plant genome can be removed by, for example, crossing with non-modified plants or segregation of non-homozygous plants.

"Transient transformation" in the context of a polynucleotide means that a polynucleotide is introduced into the cell and does not integrate into the genome of the cell.

By "stably introducing" or "stably introduced," in the context of a polynucleotide, means that the introduced polynucleotide is stably incorporated into the genome of the cell, and thus the cell is stably transformed with the polynucleotide.

"Stable transformation" or "stably transformed" as used herein means that a nucleic acid construct is introduced into a cell and integrates into the genome of the cell. As such, the integrated nucleic acid construct is capable of being inherited by the progeny thereof, more particularly, by the progeny of multiple successive generations. "Genome" as used herein can include the nuclear, plastid, and/or mitochondrial genome, and therefore may include integration of a nucleic acid construct into the nuclear, plastid and/or mitochondrial genome. Stable transformation as used herein may also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into a plant or plant cell. Stable transformation of a cell can be detected by, for example, a Southern blot hybridization assay of genomic DNA of the cell with nucleic acid sequences which specifically hybridize with a nucleotide sequence of a transgene introduced into an organism (e.g., a bacterium, an archaea, a yeast, an algae, and the like). Stable transformation of a cell can be detected by, for example, a Southern blot hybridization assay of DNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols well known in the art.

Procedures for transforming plants are well known and routine in the art and are described throughout the literature. Non-limiting examples of methods for transformation of plants include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen & Willmitzer (1988) *Nucleic Acids Res.* 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and/or plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

A nucleotide sequence therefore can be introduced into the plant, plant part and/or plant cell in any number of ways that are well known in the art. The methods of the invention do not depend on a particular method for introducing one or more nucleotide sequences into a plant, only that they gain access to the interior of at least one cell of the plant. Thus, in particular embodiments of the invention, intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

As used herein, "tobacco product" refers to a product comprising material produced by a *Nicotiana* plant, including for example, nicotine gum and patches for smoking cessation, cigarette tobacco including expanded (puffed) and reconstituted tobacco, cigar tobacco, pipe tobacco, cigarettes, cigars, and all forms of smokeless tobacco such as chewing tobacco, snuff, snus and lozenges. "Cigarettes" includes electronic cigarettes and "heat not burn" products which are cigarette-like devices that heat tobacco rather than burn tobacco. In some embodiments, a tobacco product may include but is not limited to, a cigarillo, a kretek cigarette, a non-ventilated recess filter cigarette, a vented recess filter cigarette, a cigar, snuff, a tobacco-containing gum, a tobacco-containing lozenge, and/or a chewing tobacco.

The present invention is directed in part to the discovery that a *Nicotiana* plant comprising (a) the polynucleotides that encode the Berberine Bridge Like (BBL) polypeptides, BBLa, BBLb, and BBLc, which have been modified so as to reduce or eliminate expression of the polynucleotides and/or activity of the polypeptide produced therefrom, and (b) the recessive allele of nic1, or the recessive allele of nic1 and the recessive allele of nic2 provides reduced nicotinic alkaloid content as compared to a *Nicotiana* plant that does not comprise the modified BBLa, BBLb, and BBLc polynucleotides and the recessive allele of nic1, or the recessive allele of nic1 and the recessive allele of nic2 or as compared to a *Nicotiana* plant that comprises the modified BBLa, BBLb, and BBLc polynucleotides only.

Nicotine is a highly studied plant natural product produced in significant quantities by the species *Nicotiana tabacum* L., commonly known as tobacco, and numerous other members of the *Nicotiana* genus. This pyridine alkaloid is synthesized in tobacco roots and subsequently translocated to aerial plant parts in processes stimulated by plant wounding or loss of the apical inflorescence. Nicotine accumulation likely plays a role in natural plant defense against herbivores. Nicotine also plays an important role in human society as it is the primary addictive substance in manufactured tobacco products such as combustible cigarettes which have well-studied toxicant profiles. The United States Food and Drug Administration (FDA) lists 93 tobacco and tobacco smoke chemical constituents designated as 'harmful and potentially harmful' due to their association with carcinogenesis, addiction, or respiratory, cardiovascular, reproductive, or developmental toxicity (U.S. Food and Drug Administration 2012).

Nicotine per se is not recognized as a carcinogen, but the World Health Organization (2015) and the United States Food and Drug Administration (2018) have recommended a mandated lowering of nicotine levels in combustible cigarettes to non-addictive levels in order to reduce overall addiction to such products and to lower corresponding toxicant exposure. Percent nicotine on a dry weight basis in conventional tobacco cultivars typically ranges from between 1.0 and 5.0%, with observed variability being due to market type (burley, flue-cured, dark, cigar, or Oriental), plant genetics, growing environment, and stalk position. Manufacturers blend sourced cured leaf to produce cigarette tobacco filler with between 1.0 to 2.0% nicotine on a dry weight basis. The specific concentrations at which nicotine becomes non-addictive in combustible cigarettes may be difficult to determine and may vary amongst individuals, but Benowitz and Henningfield (New Engl. J. Med. 331, 123-125 (1994)) have predicted tobacco filler nicotine contents of between 0.02 and 0.03% to be below a 'sub-threshold level of addiction.' The World Health Organization (2015) has recommended lowering of nicotine content of the tobacco filler to below 0.04%.

Various methods of chemical extraction have reportedly been used to achieve 80% to 98% reductions in nicotine content of tobacco filler. However, increased costs associated with chemical extraction, and the potential for co-extraction of compounds that positively affect organoleptic properties, make these approaches unattractive. Use of modified plant genetics is a preferred route to achieve reduced cigarette nicotine levels.

Genetic approaches to develop new tobacco cultivars with reduced potential for nicotine accumulation include the use of (1) genetic variability that naturally exists within *N. tabacum* or closely related species, (2) genetic variability induced by gene editing or mutagen treatment, or (3) novel variation generated via genetic engineering. Wide variation exists for alkaloid accumulation amongst diverse tobacco materials in the United States *Nicotiana* Germplasm Collection, ranging from 0.02 to 6.55% on a dry weight basis. The ultra-low nicotine levels of 0.04% recommended by the World Health Organization are not routinely observed amongst the lowest-alkaloid material, however. Recessive alleles at the Nic1 and Nic2 (also known as A and B) loci have been found to contribute to major reductions in nicotine and associated alkaloids (nornicotine, anabasine, and anatabine) from between 1.5 and 4.5% to approximately 0.20 to 0.45%. However, this allelic variability is well known to be associated with reduced cured leaf yields and quality, rendering the cured leaf commercially undesirable.

Knowledge of specific genes identified to be involved in nicotine biosynthesis allows for the use of technologies such as RNA interference to lower their expression and achieve corresponding reductions in nicotine accumulation. Commercialization of 'GMO' tobacco cultivars is subject to variable levels of complicating regulatory oversight around the world, however. As an alternative to genetic engineering, gene silencing achieved via induced mutation or gene editing might be used to realize reductions in nicotine. Because of the polyploid nature of *N. tabacum*, mutations in multiple gene copies are often necessary to achieve a desired phenotype. The increased complexity of mutation breeding in a polyploid species can be offset by the fact that outcomes of such breeding approaches are not considered regulated articles in many parts of the world.

The Berberine Bridge Like (BBL) gene family was previously identified to encode for enzymes involved in one of the final steps of the *N. tabacum* nicotine biosynthetic pathway, although their precise role is currently not understood. This family is comprised of six closely related members, three of which are expressed to significant degrees (BBL-a, BBL-b, and BBL-c) and three of which are lowly expressed (BBL-d1, BBL-d2, and BBL-e). We previously demonstrated substantially reduced nicotine content in conventionally field-grown flue-cured tobacco plants carrying RNA interference transgenes to reduce expression of this gene family (Lewis et al., *PLOS ONE* 10, e0117273 (2015)). We also reported preliminary results on the effect of induced mutations in the three most highly expressed BBL gene family members (Lewis et al., *PLOS ONE* 10, e0117273 (2015)). The present invention is directed to the development and testing of tobacco lines combining the BBLabc mutations with the naturally occurring recessive alleles at the Nic1 and Nic2 loci.

Accordingly, the present invention provides a method of producing a *Nicotiana* plant having reduced nicotinic alkaloid content, the method comprising combining in a *Nicotiana* plant: (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2, wherein the *Nicotiana* plant has a nicotinic alkaloid content that is reduced as compared to a plant that is modified per (A) only (e.g., not modified per (A) and (B)). In some embodiments, the method comprises combining in a *Nicotiana* plant: (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1. In some embodiments, the method comprises combining in a *Nicotiana* plant: (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 and a recessive allele of nic2. In some embodiments, the method of producing a *Nicotiana* plant having reduced nicotinic alkaloid content may further comprise modifications reducing the expression of a polynucleotide encoding an additional nicotinic alkaloid biosynthetic enzyme. In some embodiments, the additional nicotinic alkaloid biosynthetic enzyme can include, but is not limited to, aspartate oxidase, quinolinate synthase, quinolate phosphoribosyl transferase, ornithine decarboxylase, putrescine N-methyltransferase, methyl putrescine oxidase, and/or A622.

In some embodiments, a *Nicotiana* plant produced by the methods of the invention may comprise a nicotinic alkaloid content that is reduced by at least 40% (e.g., at least about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96%, or more; or any range or value therein) as compared to a plant that is modified per (A) only (e.g., not modified per (A) and (B)). In some embodiments, the nicotinic alkaloid that is reduced in the *Nicotiana* plant produced by the methods of the invention may be nicotine, wherein the nicotine content may be reduced by about 40% to about 90% (e.g., about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 or 91%, or more; or any range or value therein) as compared to a plant that is modified per (A) only (e.g., not modified per (A) and (B)). In some embodiments, the *Nicotiana* plant produced by the methods of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2 may comprise a nicotine content of about 0.014% to about $0.0^{98}\%$.

In some embodiments, a *Nicotiana* plant produced by the methods of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 may comprise a nicotinic alkaloid content that is reduced by at least about 30% (e.g., about 30, 31, 32, 33, 34, 35, 36, 37, 38, 39, 40, 41, 42, 43, 44, 45, 46, 47, 48, 49, 50, 51, 52, 53, 54, 55, 56% or more, or any range or value therein) as compared to a plant that is modified per (A) only (e.g., not modified per (A) and (B)). In some embodiments, the nicotinic alkaloid that is reduced in the *Nicotiana* plant of the invention may be nicotine, wherein the nicotine content may be reduced by about 40% as compared to a plant that is modified per (A) only (e.g., not modified per (A) and (B)). In some embodiments, the *Nicotiana* plant of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 may comprise a nicotine content of about 0.098%.

In some embodiments, a *Nicotiana* plant produced by the methods of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 and a recessive allele of nic2 may comprise a nicotinic alkaloid content that is reduced by at least about 40% (e.g., at least about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96%, or more, or any range or value therein) as compared to a plant that is modified per (A) only (e.g., not modified per (A) and (B)). In some embodiments, the nicotinic alkaloid that is reduced in the *Nicotiana* plant of the invention may be nicotine, wherein the nicotine content may be reduced by about 90% (e.g., about 90, 91, 92, 93, 94, 95, 96, 97% or more) as compared to a plant that is modified per (A) only (e.g., not modified per (A) and (B)). In some embodiments, the *Nicotiana* plant of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 and a recessive allele of nic2 may comprise a nicotine content of about 0.014%.

In some embodiments, a *Nicotiana* plant produced by the methods of the invention may comprise increased chlorophyll (e.g., increased greenness) as compared to a plant that is modified per (A) only (e.g., not modified per (A) and (B)), optionally wherein the increase in chlorophyll is in the leaves of the plant or in the leaves and the stems of the plant. In some embodiments, a *Nicotiana* plant produced by the methods of the invention may comprise a lower sugar content as compared to a plant that is modified per (A) only (e.g., not modified per (A) and (B)), optionally wherein the sugar content may be reduced by about 7%-28% (e.g., about 7, 8, 9, 10, 11, 12, 13, 14, 15, 16, 17, 18, 19, 20, 21, 22, 23, 24, 25, 26, 27, 28% or more, or any range or value therein) as compared to a plant that is modified per (A) only (e.g., not modified per (A) and (B)). In some embodiments, a *Nicotiana* plant produced by the methods of the invention may comprise a lower nitrogen content as compared to a plant that is modified per (A) only (e.g., not modified per (A) and (B)), optionally wherein the nitrogen content may be reduced by about 10%-25% (e.g., about 10, 11, 12, 13, 14, 15, 16, 17, 18, 19, 20, 21, 22, 23, 24, 25% or more, or any range or value therein) as compared to a plant that is modified per (A) only (e.g., not modified per (A) and (B)).

The present invention further provides methods of curing the leaves and stems of a *Nicotiana* plant of the present invention. The *Nicotiana* plants of the present invention that comprise the genetic modifications described herein produce leaves and stems that when cured using standard tobacco curing methods (such as, e.g, methods described in Powell 1987 (Manual entitled Powell Manufacturing, Co.'s Bulk Curing/Drying Owner's Operator's Manual for Flue Cured Tobaccos, Powell Manufacturing, Co. (Jan. 20, 1987)) do not provide a tobacco of sufficient quality for use in tobacco products. In contrast to standard methods of curing, the methods of curing described herein when applied to the leaves and stems of the *Nicotiana* plants of the present invention (e.g., having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2) provide tobacco having improved quality as compared to the leaves and stems of the *Nicotiana* plants of the present invention cured using standard curing protocols (e.g., a yellowing process comprising heating the leaf at starting temperature of about 92° F. to about 96° F. (e.g., about 92° F., 93° F., 94° F., 95° F., or 96° F. or any range or value therein) and increasing to a maximum upper temperature of about 104° F. to about 108° F. (e.g., about 104° F., 105° F., 106° F., 107° F., 108° F. or any range or value therein) at a rate of about 1° F. per hour until reaching maximum upper temperature, which upper temperature is held for about a period of about 52-58 hours (e.g, about 52, 53, 54, 55, 56 hours or any range or value therein); a leaf drying process at a temperature of about 120° F. for about 22 hours; and (c) a stem drying process at a temperature of about 132° F.-138° F. (e.g., about 132° F., 133° F., 134° F., 135° F., 136° F., 137° F., or 138° F. or any range or value therein) for about 50 hours to about 65 hours (e.g, about 50, 51, 52, 53, 54, 55, 56, 57, 58, 59, 60, 61, 62, 63, 64, or 65 hours or any range or value therein) with continuous monitoring, thereby curing the one or more leaves of the *Nicotiana* plant and producing one or more cured leaves of the *Nicotiana* plant). In some embodiments, the leaf drying process takes place at a temperature of about 116° F.-120° F. or about 116° F.-118° F. (e.g., about 116° F., 117° F., 118° F., 119° F., 120° F., or any range or value therein) for about 28-34 hours (e.g., about 28, 29, 30, 31, 32, 33, or 34 hours, or any range or value therein). Improvements in the quality of the *Nicotiana* plants of the present technology cured according to the methods of the present technology include, but are not limited to, a better index grade, improved texture, improved color, a high-good quality, increased sugar levels, and reduced ammonia levels as compared to the *Nicotiana* plants of the present technology cured using standard curing protocols. Sugar levels in a flue-cured variety are an indicator of a good flavor bright leaf, and ammonia levels are typically used as an indicator of off-taste in tobacco.

Thus, in some embodiments, the present invention provides a method of curing one or more leaves and/or stems of a *Nicotiana* plant, the *Nicotiana* plant having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2, wherein the *Nicotiana* plant has a nicotinic alkaloid content that is reduced as compared to a plant that is modified per (A) only, the method comprising: (a) a yellowing process comprising heating the leaf at a temperature starting at 92° F.-96° F. and increasing to a temperature of about 104° F.-108° F. (e.g., 104° F., 105° F., 106° F., 107° F., or 108° F., or any range or value therein) at a rate of about 1° F. per hour until reach maximum upper temperature and hold at the upper temperature for a period of about 52-58 hours (e.g., about 52, 53, 54, 55, 56, 57, or 58 hours and any range or value therein), optionally wherein the process is about 54 hours in length; (b) a leaf drying process at a temperature of about 120° F. for about 22 hours, optionally; and (c) a stem drying process at a temperature of about 132° F.-138° F. (132° F., 133° F., 134° F., 135° F., 136° F., 137° F., or 118° F., or any range or value therein), optionally 134° F., for about 50 hours to about 65 hours (e.g., about 50, 51, 52, 53, 54, 55, 56, 57, 58, 59, 6, 61, 62, 63, 64, or 65 hours, or any range of value therein) with continuous monitoring, thereby curing the one or more leaves of the *Nicotiana* plant and producing one or more cured leaves of the *Nicotiana* plant. In some embodiments, the leaf drying process takes place at a temperature of about 116° F.-120° F. or about 116° F.-118° F. (116° F., 117° F., 118° F., 119° F., 120° F., or any range or value therein) for about 28-34 hours.

In some embodiments, the present invention provides a cured tobacco produced by the methods of the invention. In some embodiments, cured tobacco of the present invention (e.g., leaf, smoking leaf, lugs, cutters, primings) has the characteristics of a fair to good quality with good color intensity, normal width and uniform texture, optionally wherein the cured tobacco has a USDA grade index of over 60. In some embodiments, the cured tobacco is of a good to fair to low quality or fine to good to fair quality per the USDA Standard Grades ("Official Standard Grades for Flue-Cured Tobacco U.S. Types 11, 12, 13, 14, and Foreign Type 92") (as published on the USDA Agriculture Marketing Service website (ams.usda.gov/grades-standards/tobacco)) and Title 7, Chapter 1, Part 29 Issued under authority of The Tobacco Inspection Act (49 Stat. 731; 7 U.S.C. 511)(effective date of Mar. 27, 1989 (54 F.R. 7925). Example USDA standard grades are described in Table 1.

TABLE 1

| Grades | Grade Name | Minimum Specifications |
|---|---|---|
| | Leaf (B Group) | Leaves normally grown at or above the midportion of the stalk. Leaves of the B group have a pointed tip, tend to fold, usually are heavier in body than the other groups, and show little or no ground injury |
| B1L | Choice Quality Lemon Leaf | Ripe, firm leaf structure, medium body, rich in oil, deep color intensity, spready, 20 inches or over in length. Uniformity, 90 percent; injury tolerance, 5 percent |
| B2L | Fine Quality Lemon Leaf | Ripe, firm leaf structure, medium body, rich in oil, deep color intensity, normal width, 18 inches or over in length. Uniformity, 85 percent; injury tolerance, 10 percent |
| B3L | Good Quality Lemon Leaf | Ripe, firm leaf structure, medium body, oily, strong color intensity, normal width, 16 inches or over in length. Uniformity, 80 percent; injury tolerance, 15 percent |
| B4L | Fair Quality Lemon Leaf | Ripe, firm leaf structure, medium body, only, moderate color intensity, normal width. Uniformity, 70 percent; injury tolerance, 20 percent of which not over 5 percent may be waste |
| B5L | Low Quality Lemon Leaf | Ripe, firm leaf structure, medium body, lean in oil, weak color intensity, narrow. Uniformity, 70 percent; injury tolerance 30 percent, of which not over 10 percent may be waste |
| B6L | Poor Quality Lemon Leaf | Ripe, firm leaf structure, medium body, lean in oil, weak color intensity, stringy. Uniformity, 70 percent; injury tolerance 40 percent, of which not over 20 percent may be waste |
| B1F | Choice Quality Orange Leaf | Ripe, firm leaf structure, fleshy, rich in oil, deep color intensity, spready, 20 inches or over in length. Uniformity, 90 percent; injury tolerance, 5 percent |
| B2F | Fine Quality Orange Leaf | Ripe, firm leaf structure, fleshy, rich in oil, deep color intensity, normal width, 18 inches or over in length. Uniformity, 85 percent; injury tolerance, 10 percent |
| B3F | Good Quality Orange Leaf | Ripe, firm leaf structure, fleshy, oily, strong color intensity, normal width, 16 inches or over in length. Uniformity, 80 percent; injury tolerance, 15 percent |
| B4F | Fair Quality Orange Leaf | Ripe, firm leaf structure, fleshy, oily, moderate color intensity, normal width. Uniformity, 70 percent; injury tolerance, 20 percent of which not over 5 percent may be waste |
| B5F | Low Quality Orange Leaf | Ripe, firm leaf structure, fleshy, lean in oil, weak color intensity, narrow. Uniformity, 70 percent; injury tolerance 30 percent, of which not over 10 percent may be waste |
| B6F | Poor Quality Orange Leaf | Ripe, firm leaf structure, fleshy, lean in oil, weak color intensity, stringy. Uniformity, 70 percent; injury tolerance 40 percent, of which not over 20 percent may be waste |
| B1FR | Choice Quality Orange Red Leaf | Ripe, firm leaf structure, fleshy, rich in oil, deep color intensity, spready, 20 inches or over in length. Uniformity, 90 percent; injury tolerance, 5 percent |
| B2FR | Fine Quality Orange Red Leaf | Ripe, firm leaf structure, fleshy, rich in oil, deep color intensity, normal width, 18 inches or over in length. Uniformity, 85 percent; injury tolerance, 10 percent |
| B3FR | Good Quality Orange Red Leaf | Ripe, firm leaf structure, fleshy, oily, strong color intensity, normal width, 16 inches or over in length. Uniformity, 80 percent; injury tolerance, 10 percent |

TABLE 1-continued

| Grades | Grade Name | Minimum Specifications |
|---|---|---|
| B4FR | Fair Quality Orange Red Leaf | Ripe, firm leaf structure, fleshy, oily, moderate color intensity, normal width. Uniformity, 70 percent; injury tolerance, 20 percent of which not over 5 percent may be waste |
| B5FR | Low Quality Orange Red Leaf | Ripe, firm leaf structure, fleshy, lean in oil, weak color intensity, narrow. Uniformity, 70 percent; injury tolerance 30 percent, of which not over 10 percent may be waste |
| B6FR | Poor Quality Orange Red Leaf | Ripe, firm leaf structure, fleshy, lean in oil, weak color intensity, stringy. Uniformity, 70 percent; injury tolerance 40 percent, of which not over 20 percent may be waste |
| B5R | Low Quality Red Leaf | Ripe, firm leaf structure, heavy, lean in oil, weak color intensity, narrow. Uniformity, 70 percent; injury tolerance 30 percent, of which not over 10 percent may be waste |
| B3K | Good Quality Variegated Leaf | Ripe, firm leaf structure, fleshy, oily, normal width, 16 inches or over in length. Uniformity, 80 percent; injury tolerance, 15 percent |
| B4K | Fair Quality Variegated Leaf | Ripe, firm leaf structure, fleshy, lean in oil, normal width. Uniformity, 70 percent; injury tolerance, 20 percent of which not over 5 percent may be waste |
| B5K | Low Quality Variegated Leaf | Ripe, firm leaf structure, fleshy, lean in oil, narrow. Uniformity, 70 percent; injury tolerance 30 percent, of which not over 10 percent may be waste |
| B6K | Poor Quality Variegated Leaf | Ripe, firm leaf structure, fleshy, lean in oil, stringy. Uniformity, 70 percent; injury tolerance 40 percent, of which not over 20 percent may be waste. |
| B2KR | Good Quality Variegated Red or Scorched Leaf | Ripe, firm leaf structure, fleshy, oily, normal width, 16 inches or over in length. Uniformity, 80 percent; injury tolerance 15 percent. |
| B4KR | Fair Quality Variegated Red or Scorched Leaf | Ripe, firm leaf structure, fleshy, lean in oil, normal width. Uniformity, 70 percent; injury tolerance 20 percent, of which not over 5 percent may be waste |
| B5KR | Low Quality Variegated Red or Scorched Leaf | Ripe, firm leaf structure, fleshy, lean in oil, narrow. Uniformity, 70 percent; injury tolerance 30 percent, of which not over 10 percent may be waste |
| B3V | Good Quality Greenish Leaf | Mature, firm leaf structure, fleshy, oily, normal width, 16 inches or over in length. Uniformity, 80 percent; injury tolerance 15 percent |
| B4V | Fair Quality Greenish Leaf | Mature, firm leaf structure, fleshy, oily, normal width. Uniformity, 70 percent; injury tolerance 20 percent of which not over 5 percent may be waste |
| B5V | Poor Quality Greenish Leaf | Mature, firm leaf structure, fleshy, lean in oil, narrow. Uniformity, 70 percent; injury tolerance 30 percent, of which not over 10 percent may be waste |
| B3KL | Good Quality Variegated Lemon Leaf | Unripe, close leaf structure, heavy, normal width, 16 inches or over in length. Uniformity, 80 percent; injury tolerance, 15 percent |
| B4KL | Fair Quality Variegated Lemon Leaf | Unripe, close leaf structure, heavy, normal width. Uniformity, 70 percent; injury tolerance 20 percent of which not over 5 percent may be waste |
| B5KL | Low Quality Variegated Lemon Leaf | Unripe, tight leaf structure, heavy, narrow. Uniformity, 70 percent; injury tolerance 30 percent, of which not over 10 percent may be waste |

TABLE 1-continued

| Grades | Grade Name | Minimum Specifications |
|---|---|---|
| B6KL | Poor Quality Variegated Lemon Leaf | Unripe, tight leaf structure, heavy, stringy. Uniformity, 70 percent; injury tolerance 40 percent, of which not over 20 percent may be waste |
| B3KF | Good Quality Variegated Orange Leaf | Unripe, close leaf structure, heavy, normal width, 16 inches or over in length. Uniformity, 80 percent; injury tolerance, 15 percent |
| B4KF | Fair Quality Variegated Orange Leaf | Unripe, close leaf structure, heavy, normal width. Uniformity, 70 percent; injury tolerance 20 percent, of which not over 5 percent may be waste |
| B5KF | Low Quality Variegated Orange Leaf | Unripe, tight leaf structure, heavy, narrow. Uniformity, 70 percent; injury tolerance 30 percent, of which not over 10 percent may be waste |
| B6KF | Poor Quality Variegated Orange Leaf | Unripe, tight leaf structure, heavy, stringy. Uniformity, 70 percent; injury tolerance 40 percent, of which not over 20 percent may be waste |
| B3KD | Good Quality Variegated Dark Red Leaf | Unripe, close leaf structure, heavy, normal width, 16 inches (40.6 cm) or over in length. Uniformity, 80 percent; injury tolerance, 15 percent |
| B4KD | Fair Quality Variegated Dark Red Leaf | Unripe, close leaf structure, heavy, normal width. Uniformity, 70 percent; injury tolerance 20 percent, of which not over 5 percent may be waste |
| B5KD | Low Quality Variegated Dark Red Leaf | Unripe, tight leaf structure, heavy, narrow. Uniformity, 70 percent; injury tolerance 30 percent, of which not over 10 percent may be waste |
| B6KD | Poor Quality Variegated Dark Red Leaf | Unripe, tight leaf structure, heavy, stringy. Uniformity, 70 percent; injury tolerance 40 percent, of which not over 20 percent may be waste |
| B3KM | Good Quality Variegated Mixed Leaf | Unripe, close leaf structure, heavy, normal width, 16 inches or over in length. Uniformity, 80 percent; injury tolerance, 15 percent |
| B4KM | Fair Quality Variegated Mixed Leaf | Unripe, close leaf structure, heavy, normal width. Uniformity, 70 percent; injury tolerance 20 percent, of which not over 5 percent may be waste |
| B5KM | Low Quality Variegated Mixed Leaf | Unripe, tight leaf structure, heavy, narrow. Uniformity, 70 percent; injury tolerance 30 percent, of which not over 10 percent may be waste |
| B6KM | Poor Quality Variegated Mixed Leaf | Unripe, tight leaf structure, heavy, stringy. Uniformity, 70 percent; injury tolerance 40 percent, of which not over 20 percent may be waste |
| B3KK | Good Quality Excessively Scorched Leaf | Unripe, close leaf structure, heavy, normal width, 16 inches (40.6 cm) or over in length. Uniformity, 80 percent; injury tolerance, 15 percent |
| B4KK | Fair Quality Excessively Scorched Leaf | Unripe, close leaf structure, heavy, normal width. Uniformity, 70 percent; injury tolerance 20 percent, of which not over 5 percent may be waste |
| B5KK | Low Quality Excessively Scorched Leaf | Unripe, tight leaf structure, heavy, narrow. Uniformity, 70 percent; injury tolerance 30 percent, of which not over 10 percent may be waste |
| B6KK | Poor Quality Excessively Scorched Leaf | Unripe, tight leaf structure, heavy, stringy. Uniformity, 70 percent; injury tolerance 40 percent, of which not over 20 percent may be waste |
| B4KV | Fair Quality Variegated Greenish Leaf | Unripe, firm leaf structure, medium body, normal width. Uniformity, 70 percent; tolerance, 25 percent waste |
| B5KV | Low Quality Variegated Greenish Leaf | Unripe, firm leaf structure, medium body, narrow. Uniformity, 70 percent; tolerance, 30 percent waste |
| B6KV | Poor Quality Variegated Greenish Leaf | Unripe, firm leaf structure, medium body, stringy. Uniformity, 70 percent; tolerance, 40 percent waste |

TABLE 1-continued

| Grades | Grade Name | Minimum Specifications |
|---|---|---|
| B3S | Good Quality Slick Leaf | Unripe, close leaf structure, fleshy, normal width, 16 inches or over in length. Uniformity, 80 percent; injury tolerance, 15 percent |
| B4S | Fair Quality Slick Leaf | Unripe, close leaf structure, fleshy, normal width. Uniformity, 70 percent; injury tolerance, 20 percent, of which not over 5 percent may be waste |
| B5S | Low Quality Slick Leaf | Unripe, tight leaf structure, fleshy, narrow. Uniformity, 70 percent; injury tolerance 30 percent, of which not over 10 percent may be waste |
| B4G | Fair Quality Green Leaf | Immature, close leaf structure, fleshy, oily, normal width. Uniformity, 70 percent; injury tolerance 20 percent, of which not over 5 percent may be waste |
| B5G | Low Quality Green Leaf | Immature, tight leaf structure, fleshy, lean in oil, narrow. Uniformity, 70 percent; injury tolerance 30 percent, of which not over 10 percent may be waste |
| B6G | Poor Quality Green Leaf | Immature, tight leaf structure, fleshy, lean in oil, stringy. Uniformity, 70 percent; injury tolerance 40 percent, of which not over 20 percent may be waste |
| B5GR | Low Quality Green Red Leaf | Immature, tight leaf structure, heavy, lean in oil, narrow. Uniformity, 70 percent; injury tolerance 30 percent, of which not over 10 percent may be waste |
| B4GK | Fair Quality Green Variegated Leaf | Immature, close leaf structure, heavy, normal width. Uniformity, 70 percent; injury tolerance 20 percent, of which not over 5 percent may be waste |
| B5GK | Low Quality Green Variegated Leaf | Immature, tight leaf structure, heavy, narrow. Uniformity, 70 percent; injury tolerance 30 percent, of which not over 10 percent may be waste |
| B6GK | Poor Quality Green Variegated Leaf | Immature, tight leaf structure, heavy, stringy. Uniformity, 70 percent; injury tolerance 40 percent, of which not over 20 percent may be waste |
| B5GG | Low Quality Gray Green Leaf | Immature, tight leaf structure, heavy, narrow. Uniformity, 70 percent; injury tolerance 30 percent, of which not over 10 percent may be waste |
| Smoking Leaf (H Group) | | Leaves normally grown at or above the midportion of the stalk. Leaves of the H group show a high degree of maturity, more open leaf structure in relation to the B Group, and a material amount of injury characteristic of very ripe leaf tobacco |
| H3F | Good Quality Orange Smoking Leaf | Mellow, open leaf structure, medium body, lean in oil, strong color intensity, normal width, 16 inches or over in length. Uniformity, 80 percent; injury tolerance, 15 percent |
| H4F | Fair Quality Orange Smoking Leaf | Mellow, open leaf structure, medium body, lean in oil, moderate color intensity, normal width. Uniformity, 70 percent; injury tolerance, 20 percent, of which not over 5 percent may be waste |
| H5F | Low Quality Orange Smoking Leaf | Mellow, open leaf structure, medium body, lean in oil, weak color intensity, narrow. Uniformity, 70 percent; injury tolerance 30 percent, of which not over 10 percent may be waste. |
| H6F | Poor Quality Orange Smoking Leaf | Mellow, open leaf structure, medium body, lean in oil, weak color intensity, stringy. Uniformity, 70 percent; injury tolerance 40 percent, of which not over 20 percent may be waste |

TABLE 1-continued

| Grades | Grade Name | Minimum Specifications |
|---|---|---|
| H4FR | Fair Quality Orange Red Smoking Leaf | Mellow, open leaf structure, fleshy, lean in oil, moderate color intensity, normal width. Uniformity, 70 percent; injury tolerance 20 percent, of which not over 5 percent may be waste |
| H5FR | Low Quality Orange Red Smoking Leaf | Mellow, open leaf structure, fleshy, lean in oil, weak color intensity, narrow. Uniformity, 70 percent; injury tolerance 30 percent, of which not over 10 percent may be waste |
| H6FR | Poor Quality Orange Red Smoking Leaf | Mellow, open leaf structure, medium body, lean in oil, weak color intensity, stringy. Uniformity, 70 percent; injury tolerance 40 percent, of which not over 20 percent may be waste |
| H4K | Fair Quality Variegated Smoking Leaf | Mellow, open leaf structure, medium body, lean in oil, moderate color intensity, normal width. Uniformity, 70 percent; injury tolerance 20 percent, of which not over 5 percent may be waste |
| H5K | Low Quality Variegated Smoking Leaf | Mellow, open leaf structure, medium body, lean in oil, weak color intensity, narrow. Uniformity, 70 percent; injury tolerance 30 percent, of which not over 10 percent may be waste |
| H6K | Poor Quality Variegated Smoking Leaf | Mellow, open leaf structure, medium body, lean in oil, weak color intensity, narrow. Uniformity, 70 percent; injury tolerance 30 percent, of which not over 10 percent may be waste |
| | Cutters (C Group) | Leaves normally grown at or just below the midportion of the stalk. Leaves of the C group have a tendency to roll concealing the stem or midrib. Cutters usually have a rounded tip, are thin to medium in body, and show some ground injury |
| C1L | Choice Quality Lemon Cutters | Ripe, open leaf structure, medium body, oily, deep color intensity, spready, 20 inches or over in length. Uniformity, 90 percent; injury tolerance, 5 percent |
| C2L | Fine Quality Lemon Cutters | Ripe, open leaf structure, thin, oily, deep color intensity, spready, 20 inches or over in length. Uniformity, 85 percent; injury tolerance, 10 percent |
| C3L | Good Quality Lemon Cutters | Ripe, open leaf structure, thin, oily, strong color intensity, spready, 18 inches or over in length. Uniformity, 80 percent; injury tolerance, 15 percent |
| C4L | Fair Quality Lemon Cutters | Ripe, open leaf structure, thin, lean in oil, moderate color intensity, normal width, 16 inches or over in length. Uniformity, 70 percent; injury tolerance 20 percent, of which not over 5 percent may be waste. |
| C5L | Low Quality Lemon Cutters | Ripe, open leaf structure, thin, lean in oil, weak color intensity, normal width, 16 inches or over in length. Uniformity, 70 percent; injury tolerance 30 percent, of which not over 10 percent may be waste |
| C4LL | Fair Quality Whitish-Lemon Cutters | Unripe, firm leaf structure, thin (papery), lean in oil, normal width, 16 inches or over in length. Uniformity, 70 percent; injury tolerance 20 percent, of which not over 5 percent may be waste |
| C5LL | Low Quality Whitish-Lemon Cutters | Unripe, firm leaf structure, thin (papery), lean in oil, normal width, 16 inches (40.6 cm) or over in length. Uniformity, 70 percent; injury tolerance 30 percent, of which not over 10 percent may be waste |
| C5LP | Low Quality Lemon Cutters (Primings Side) | Prematurely ripe, open leaf structure, thin, lean in oil, pale color intensity, normal width, 16 inches or over in length. Uniformity, 70 percent; injury tolerance 30 percent, of which not over 10 percent may be waste |

TABLE 1-continued

| Grades | Grade Name | Minimum Specifications |
|---|---|---|
| C1F | Choice Quality Orange Cutters | Ripe, open leaf structure, medium body, oily, deep color intensity, spready, 20 inches or over in length. Uniformity, 90 percent; injury tolerance, 5 percent |
| C2F | Fine Quality Orange Cutters | Ripe, open leaf structure, medium body, oily, deep color intensity, spready, 20 inches or over in length. Uniformity, 85 percent; injury tolerance, 10 percent |
| C3F | Good Quality Orange Cutters | Ripe, open leaf structure, medium body, oily, strong color intensity, spready, 18 inches or over in length. Uniformity, 80 percent; injury tolerance, 15 percent |
| C4F | Fair Quality Orange Cutters | Ripe, open leaf structure, medium body, lean in oil, moderate color intensity, normal width, 16 inches or over in length. Uniformity, 70 percent; injury tolerance 20 percent, of which not over 5 percent may be waste |
| C5F | Low Quality Orange Cutters | Ripe, open leaf structure, medium body, lean in oil, weak color intensity, normal width, 16 inches or over in length. Uniformity, 70 percent; injury tolerance 30 percent, of which not over 10 percent may be waste |
| C5FP | Low Quality Orange Cutters (Primings Side) | Prematurely ripe, open leaf structure, medium body, lean in oil, pale color intensity, normal width, 16 inches or over length. Uniformity, 70 percent; injury tolerance 30 percent, or which not over 10 percent may be waste |
| C4KR | Fair Quality Variegated Red or Scorched Cutters | Ripe, open leaf structure, medium body, lean in oil, moderate color intensity, normal width, 16 inches or over in length. Uniformity, 70 percent; injury tolerance 20 percent, of which not over 5 percent may be waste |
| C4V | Fair Quality Greenish Cutters | Mature, open leaf structure, medium body, lean in oil, normal width, 16 inches or over in length. Uniformity, 70 percent; injury tolerance 20 percent, of which not over 5 percent may be waste |
| C4KL | Fair Quality Variegated Lemon Cutters | Unripe, close leaf structure, medium body, normal width, 16 inches or over in length. Uniformity, 70 percent; injury tolerance 20 percent, of which not over 5 percent may be waste |
| C4KF | Fair Quality Variegated Orange Cutters | Unripe, close leaf structure, medium body, normal width, 16 inches or over in length. Uniformity, 70 percent; injury tolerance 20 percent, of which not over 5 percent may be waste |
| C4KM | Fair Quality Variegated Mixed Cutters | Unripe, close leaf structure, medium body, normal width, 16 inches or over in length. Uniformity, 70 percent; injury tolerance 20 percent, of which not over 5 percent may be waste |
| C4KK | Fair Quality Excessively Scorched Cutters | Unripe, close leaf structure, medium body, normal width, 16 inches (40.6 cm) or over in length. Uniformity, 70 percent; injury tolerance, 20 percent, of which not over 5 percent may be waste |
| C4S | Fair Quality Slick Cutters | Unripe, close leaf structure, medium body, normal width, 16 inches or over in length. Uniformity, 70 percent; injury tolerance 20 percent, of which not over 5 percent may be waste |
| C4G | Fair Quality Green Cutters | Immature, close leaf structure, medium body, lean in oil, normal width, 16 inches or over in length. Uniformity, 70 percent; injury tolerance 20 percent, of which not over 5 percent may be waste |
| C4GK | Fair Quality Green Variegated Cutters | Immature, close leaf structure, medium body, normal width, 16 inches or over in length. Uniformity, 70 percent; injury tolerance 20 percent, of which not over 5 percent may be waste |

TABLE 1-continued

| Grades | Grade Name | Minimum Specifications |
|---|---|---|
| Lugs (X Group) | | Leaves normally grown near the bottom of the stalk. Leaves of the X group usually have a blunt tip and open face; they show some ground injury characteristic of the group |
| X1L | Choice Quality Lemon Lugs | Ripe, open leaf structure, thin, oily, strong color intensity.<br>Uniformity, 80 percent;<br>injury tolerance 20 percent, of which not over 5 percent may be waste |
| X2L | Fine Quality Lemon Lugs | Ripe, open leaf structure, thin, oily, strong color intensity.<br>Uniformity, 75 percent;<br>injury tolerance 25 percent, of which not over 10 percent may be waste |
| X3L | Good Quality Lemon Lugs | Ripe, open leaf structure, thin, lean in oil, moderate color intensity. Uniformity, 70 percent;<br>injury tolerance 40 percent, of which not over 20 percent may be waste |
| X4L | Fair Quality Lemon Lugs | Ripe, open leaf structure, thin, lean in oil, weak color intensity.<br>Uniformity, 70 percent;<br>tolerance, 30 percent waste |
| X5L | Low Quality Lemon Lugs | Ripe, open leaf structure, thin, lean in oil, pale color intensity.<br>Uniformity, 70 percent;<br>tolerance, 40 percent waste |
| X3LL | Good Quality Whitish-Lemon Lugs | Unripe, firm leaf structure, thin (papery), lean in oil. Uniformity, 70 percent;<br>injury tolerance 40 percent, of which not over 20 percent may be waste |
| X4LL | Fair Quality Whitish-Lemon Lugs | Unripe, firm leaf structure, thin (papery), lean in oil. Uniformity, 70 percent;<br>tolerance, 30 percent waste |
| X1F | Choice Quality Orange Lugs | Ripe, open leaf structure, medium body, oily, strong color intensity. Uniformity, 80 percent;<br>injury tolerance 20 percent, of which not over 5 percent may be waste |
| X2F | Fine Quality Orange Lugs | Ripe, open leaf structure, medium body, oily, strong color intensity. Uniformity, 75 percent;<br>injury tolerance 25 percent, of which not over 10 percent may be waste |
| X3F | Good Quality Orange Lugs | Ripe, open leaf structure, medium body, lean in oil, moderate color intensity.<br>Uniformity, 70 percent;<br>injury tolerance 40 percent, of which not over 20 percent may be waste |
| X4F | Fair Quality Orange Lugs | Ripe, open leaf structure, medium body, lean in oil, weak color intensity.<br>Uniformity, 70 percent;<br>tolerance, 30 percent waste |
| X5F | Low Quality Orange Lugs | Ripe, open leaf structure, medium body, lean in oil, pale color intensity.<br>Uniformity, 70 percent;<br>tolerance, 40 percent waste |
| X3KR | Good Quality Variegated Red or Scorched Lugs | Ripe, open leaf structure, medium body, lean in oil, moderate color intensity.<br>Uniformity, 70 percent;<br>injury tolerance 40 percent, of which not over 20 percent may be waste |
| X4KF | Fair Quality Variegated Red or Scorched Lugs | Ripe, open leaf structure, medium body, lean in oil, weak color intensity.<br>Uniformity, 70 percent;<br>tolerance, 30 percent waste |
| X3V | Good Quality Greenish Lugs | Mature, open leaf structure, medium body, lean in oil.<br>Uniformity, 70 percent;<br>injury tolerance 40 percent, of which not over 20 percent may be waste |
| X4V | Fair Quality Greenish Lugs | Mature, open leaf structure, medium body, lean in oil.<br>Uniformity, 70 percent;<br>tolerance, 30 percent waste |
| X4KL | Fair Quality Variegated Lemon Lugs | Unripe, close leaf structure, thin. Uniformity, 70 percent;<br>tolerance, 30 percent waste |
| X4KF | Fair Quality Variegated Orange Lugs | Unripe, close leaf structure, medium body. Uniformity, 70 percent;<br>tolerance, 30 percent waste |

TABLE 1-continued

| Grades | Grade Name | Minimum Specifications |
|---|---|---|
| X4KV | Fair Quality Variegated Greenish Lugs | Unripe, firm leaf structure, medium body. Uniformity, 70 percent; tolerance, 30 percent waste |
| X3KM | Good Quality Variegated Mixed Lugs | Unripe, close leaf structure, medium body. Uniformity, 70 percent; injury tolerance 40 percent, of which not over 20 percent may be waste |
| X4KM | Fair Quality Variegated Mixed Lugs | Unripe, close leaf structure, medium body. Uniformity, 70 percent; tolerance, 30 percent waste |
| X3S | Good Quality Slick Lugs | Unripe, close leaf structure, medium body. Uniformity, 70 percent; injury tolerance 40 percent, of which not over 20 percent may be waste |
| X4S | Fair Quality Slick Lugs | Unripe, close leaf structure, medium body. Uniformity, 70 percent; tolerance, 30 percent waste |
| X4G | Fair Quality Green Lugs | Immature, firm leaf structure, medium body, lean in oil. Uniformity, 70 percent; tolerance, 30 percent waste |
| X5G | Low Quality Green Lugs | Immature, firm leaf structure, medium body, lean in oil. Uniformity, 70 percent; tolerance, 40 percent waste |
| X4GK | Fair Quality Green Variegated Lugs | Immature, close leaf structure, medium body. Uniformity, 70 percent; tolerance, 30 percent waste |
| | Primings (P Group) | Leaves from the lowest portion of the stalk. Leaves of the P group ripen prematurely as a result of starvation and show a material amount of injury characteristic of leaves grown close to the ground |
| P2L | Fine Quality Lemon Primings | Prematurely ripe, open leaf structure, thin, oily, moderate color intensity. Uniformity, 75 percent; injury tolerance 25 percent, of which not over 10 percent may be waste |
| P3L | Good Quality Lemon Primings | Prematurely ripe, open leaf structure, thin, lean in oil, weak color intensity. Uniformity, 70 percent; injury tolerance 40 percent, of which not over 20 percent may be waste |
| P4L | Fair Quality Lemon Primings | Prematurely ripe, open leaf structure, thin, lean in oil, pale color intensity. Uniformity, 70 percent; tolerance, 30 percent waste |
| P5L | Low Quality Lemon Primings | Prematurely ripe, open leaf structure, thin, lean in oil, pale color intensity. Uniformity, 70 percent; tolerance, 40 percent waste |
| P2F | Fine Quality Orange Primings | Prematurely ripe, open leaf structure, medium body, oily, moderate color intensity. Uniformity, 75 percent; injury tolerance 25 percent, of which not over 10 percent may be waste |
| P3F | Good Quality Orange Primings | Prematurely ripe, open leaf structure, medium body, lean in oil, weak color intensity. Uniformity, 70 percent; injury tolerance 40 percent, of which not over 20 percent may be waste |
| P4F | Fair Quality Orange Primings | Prematurely ripe, open leaf structure, medium body, lean in oil, pale color intensity. Uniformity, 70 percent; tolerance, 30 percent waste |
| P5F | Low Quality Orange Primings | Prematurely ripe, open leaf structure, medium body, lean in oil, pale color intensity. Uniformity, 70 percent; tolerance, 40 percent waste |
| P4G | Fair Quality Green Primings | Immature, firm leaf structure, medium body, lean in oil. Uniformity, 70 percent; tolerance, 30 percent waste |
| P5G | Low Quality Green Primings | Immature, firm leaf structure, medium body, lean in oil. Uniformity, 70 percent; tolerance, 40 percent waste |

TABLE 1-continued

| Grades | Grade Name | Minimum Specifications |
|---|---|---|
| | Mixed (M group) | Tobacco from three or more groups or two distinctly different groups which are mixed together in various combinations |
| M4F | Fair Quality Mixed Groups | Ripe, firm leaf structure, heavy, lean in oil. Injury tolerance 30 percent, of which not over 10 percent may be waste |
| M5F | Low Quality Mixed Groups | Ripe, firm leaf structure, heavy, lean in oil. Injury tolerance 40 percent, of which not over 20 percent may be waste |
| M4KF | Fair Quality Variegated Red or Scorched Mixed Groups | Ripe, firm leaf structure, fleshy, lean in oil. Injury tolerance 30 percent, of which not over 10 percent may be waste |
| M4KM | Fair Quality Variegated Mixed Groups | Unripe, close leaf structure, heavy. Injury tolerance 30 percent, of which not over 10 percent may be waste |
| M5KM | Low Quality Variegated Mixed Groups | Unripe, tight leaf structure, heavy. Injury tolerance 40 percent, of which not over 20 percent may be waste |
| M4GK | Fair Quality Green Variegated Mixed Groups | Immature, close leaf structure, heavy. Injury tolerance 30 percent, of which not over 10 percent may be waste |
| M5GK | Low Quality Green Variegated Mixed Groups | Immature, tight leaf structure, heavy. Injury tolerance, 40 percent, of which not over 20 percent may be waste |

In some embodiments, a cured tobacco leaf from a *Nicotiana* plant is provided, wherein (A) the *Nicotiana* plant (1) comprises one or both of the recessive nic1 and nic2 alleles and (2) comprises BBLa, BBLb, and BBLc genes that are altered, relative to wild type, such that the nicotinic alkaloid content of the *Nicotiana* plant is reduced compared to said wild type; and (B) the cured tobacco leaf (including leaf, smoking leaf, tips, cutter, lugs) has the characteristics of good to fair quality leaf with good color intensity, normal width and uniform texture, in comparison to leaf from the same *Nicotiana* plant that is not cultivated and cured using a the methods of the present invention and thereby producing a poor to low quality leaf. In some embodiments, a cured tobacco of this invention may have a USDA grade index of over 60.

In some embodiments, a cured tobacco produced by the methods of the invention from a *Nicotiana* plant the *Nicotiana* plant having one or both of the recessive nic1 and nic2 alleles and the altered BBLa, BBLb, and BBLc genes (relative to wild type) (wherein the nicotinic alkaloid content of the *Nicotiana* plant is reduced compared to said wild type) may include, but is not limited to, a leaf, a smoking leaf, tips, cutters, primings, and/or lugs. In some embodiments, a smoking leaf provided by the present invention may have a USDA quality grade of H3F (Good Quality Orange Smoking Leaf) to 4F (Fair Quality Orange Smoking Leaf) to 5F (Low Quality Orange Smoking Leaf) as compared to H6F (Poor Quality Orange Smoking Leaf) to H6FR (Poor Quality Orange Red Smoking Leaf) to H6K (Poor Quality Variegated Smoking Leaf) for a smoking leaf of a *Nicotiana* plant having one or both of the recessive nic1 and nic2 alleles and the altered BBLa, BBLb, and BBLc genes that has not been cured or cultivated using the methods of the invention. In some embodiments, a leaf (B group) provided by the present invention may have a USDA quality grade of B2L (Fine Quality Lemon Leaf) to B3L (Good Quality Lemon Leaf) to B4L (Fair Quality Lemon Leaf) as compared to B5L (Low Quality Lemon Leaf) to B6L (Poor Quality Lemon Leaf) for a leaf (B Group) of a *Nicotiana* plant having one or both of the recessive nic1 and nic2 alleles and the altered BBLa, BBLb, and BBLc genes that has not been cured or cultivated using the methods of the invention.

In some embodiments, cutters (C Group) provided by the present invention may have a USDA quality grade of C2L (Fine Quality Lemon Cutters) to C3L (Good Quality Lemon Cutters) to C4L (Fair Quality Lemon Cutters) as compared to C5L (Low Quality Lemon Cutters) for cutters (C Group) of a *Nicotiana* plant having one or both of the recessive nic1 and nic2 alleles and the altered BBLa, BBLb, and BBLc genes that has not been cured or cultivated using the methods of the invention. In some embodiments, cutters (C Group) provided by the present invention may have a USDA quality grade of C2F (Fine Quality Orange Cutters) to C3F (Good Quality Orange Cutters) to C4F (Fair Quality Orange Cutters) as compared to C5F (Low Quality Orange Cutters) for cutters (C Group) of a *Nicotiana* plant having one or both of the recessive nic1 and nic2 alleles and the altered BBLa, BBLb, and BBLc genes that has not been cured or cultivated using the methods of the invention.

In some embodiments, lugs (X Group) provided by the present invention may have a USDA quality grade of X2L (Fine Quality Lemon Lugs) to X3L (Good Quality Lemon Lugs) to X4L (Fair Quality Lemon Lugs) as compared to X5L (Low Quality Lemon Lugs) for lugs (X Group) of a *Nicotiana* plant having one or both of the recessive nic1 and nic2 alleles and the altered BBLa, BBLb, and BBLc genes that has not been cured or cultivated using the methods of the invention. In some embodiments, lugs (X Group) provided by the present invention may have a USDA quality grade of X2F (Fine Quality Orange Lugs) to X3F (Good Quality Orange Lugs) to X4F (Fair Quality Orange Lugs) as compared to X5F (Low Quality Orange Lugs) for lugs (X Group) of a *Nicotiana* plant having one or both of the recessive nic1 and nic2 alleles and the altered BBLa, BBLb, and BBLc genes that has not been cured or cultivated using the methods of the invention.

In some embodiments, primings (P Group) provided by the present invention may have a USDA quality grade of P2L (Fine Quality Lemon Primings) to P3L (Good Quality Lemon Primings) to P4L (Fair Quality Lemon Primings) as compared to P5L (Low Quality Lemon Primings) for primings (P Group) of a *Nicotiana* plant having one or both of the recessive nic1 and nic2 alleles and the altered BBLa, BBLb, and BBLc genes that has not been cured or cultivated using the methods of the invention. In some embodiments, primings (P Group) provided by the present invention may have a USDA quality grade of P2F (Fine Quality Orange Primings) to P3F (Good Quality Orange Primings) to P4F (Fair Quality Orange Primings) as compared to P5F (Low Quality Orange Primings) for primings (P Group) of a *Nicotiana* plant having one or both of the recessive nic1 and nic2 alleles and the altered BBLa, BBLb, and BBLc genes that has not been cured or cultivated using the methods of the invention.

As used herein, "leaf" refers to the major component of the tobacco plant, wherein the size, shape, and position on the stalk may be indicators of quality of the leaf. "Leaf" on a flue-cured tobacco plant refers to the second grouping of leaves from the top, whereas, in fire-cured and dark air-cured tobacco, a "leaf" is a general term for all of the leaves located in the top third of the tobacco plant.

A "smoking leaf" grows just above the middle of the stalk.

As used herein, "lugs" refers to the second grouping of leaves from the ground on a flue-cured tobacco plant; the largest leaves on a burley tobacco plant, which are located near the middle of the stalk and/or the middle grouping of leaves on fire-cured and dark air-cured tobacco plants.

A "cutters," as used herein, refers to the largest leaves on a flue-cured tobacco plant, which are located near the middle of the stalk.

As used herein, "tips" refers to the uppermost leaves on a flue-cured tobacco plant or a burley tobacco plant, and/or the pointed ends of tobacco leaves (located farthest from the stalk) that are often removed during processing.

In some embodiments, a tobacco product is provided comprising tobacco from a *Nicotiana* plant, the *Nicotiana* plant comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2, wherein the *Nicotiana* plant has a nicotinic alkaloid content that is reduced as compared to a plant that is modified per (A) only (e.g., not modified per (A) and (B)). In some embodiments, a tobacco product is provided comprising tobacco from a *Nicotiana* plant, the *Nicotiana* plant comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1. In some embodiments, a tobacco product is provided comprising tobacco from a *Nicotiana* plant, the *Nicotiana* plant comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 and a recessive allele of nic2.

In some embodiments, the *Nicotiana* plant of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2 for use in producing a tobacco product may comprise a nicotinic alkaloid content that is reduced by at least about 40% (e.g., at least about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96%, or more, or any range or value therein) as compared to a plant that is modified per (A) only (e.g., not modified per (A) and (B)). In some embodiments, the nicotinic alkaloid that is reduced in the *Nicotiana* plant of the invention for use in producing a tobacco product may be nicotine, wherein the nicotine content may be reduced by about 40% to about 90% (e.g., about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 or 91%, or more; or any range or value therein) as compared to a plant that is modified per (A) only (e.g., not modified per (A) and (B)). In some embodiments, the *Nicotiana* plant of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2 for use in producing a tobacco product may comprise a nicotine content of about 0.014% to about 0.098%.

In some embodiments, the *Nicotiana* plant of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 for use in producing a tobacco product may comprise a nicotinic alkaloid content that is reduced by at least about 30% (e.g., about 30, 31, 32, 33, 34, 35, 36, 37, 38, 39, 40, 41, 42, 43, 44, 45, 46, 47, 48, 49, 50, 51, 52, 53, 54, 55, 56% or more, or any range or value therein) as compared to a plant that is modified per (A) only (e.g., not modified per (A) and (B)). In some embodiments, the nicotinic alkaloid that is reduced in the *Nicotiana* plant of the invention for use in producing a tobacco product may be nicotine, wherein the nicotine content may be reduced by about 40% as compared to a plant that is modified per (A) only. In some embodiments, the *Nicotiana* plant of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 for use in producing a tobacco product may comprise a nicotine content of about 0.098%.

In some embodiments, the *Nicotiana* plant of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 and a recessive allele of nic2 for use in producing a tobacco product may comprise a nicotinic alkaloid content that is reduced by at least 40% (e.g., at least about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96%, or more, or any range or value therein) as compared to a plant that is modified per (A) only (e.g., not modified per (A) and (B)). In some embodiments, the nicotinic alkaloid that is reduced in the *Nicotiana* plant of the invention for use in producing a tobacco product may be nicotine, wherein the nicotine content may be reduced by about 90% (e.g., about 90, 91, 92, 93, 94, 95, 96, 97% or more or any range or value therein) as compared to a plant that is modified per (A) only. In some embodiments, the *Nicotiana* plant of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 and a recessive allele of nic2 for use in producing a tobacco product may comprise a nicotine content of about 0.014%.

Procedures for determining nicotinic alkaloid content are well known and routine in the art and are described throughout the literature. Non-limiting examples of such methods include gas chromatography, mass spectrometry (Domino et al. 1992 *Med Sci Res.* 20:859-860; Sheen et al. 2006 *J Food Sci* 53(5):1572-1573), IPLC (Keinanen et al. 2001 *J Agric Food Chem* 49:3553-3558; Halitschke and Baldwin 2003 *Plant J* 36: 794-807), UV absorption (Willits et al. 2005 *Analytical Chemistry* 22:430-433), and the like.

In some embodiments, a *Nicotiana* plant useful for producing tobacco and tobacco products as described herein may comprise further genetic modifications. For example, the *Nicotiana* plant may further comprise reduced expression of a polynucleotide encoding an additional nicotinic alkaloid biosynthetic enzyme. In some embodiments, the additional nicotinic alkaloid biosynthetic enzyme can include, but is not limited to, aspartate oxidase, quinolinate synthase, quinolate phosphoribosyl transferase, ornithine decarboxylase, putrescine N-methyltransferase, methyl putrescine oxidase, and/or A622.

A *Nicotiana* plant of the present invention may be further modified so as to reduce the activity of additional nicotinic alkaloid biosynthetic enzymes or reduce the expression of nucleic acids encoding the additional nicotinic alkaloid biosynthetic enzymes. Such additional nicotinic alkaloid biosynthetic enzymes include, but are not limited to, additional berberine bridge enzyme-like polypeptide, aspartate oxidase, quinolinate synthase, quinolate phosphoribosyl transferase, ornithine decarboxylase, putrescine N-methyltransferase, methyl putrescine oxidase, and A622. Thus, for example, the *Nicotiana* plant may be further modified to reduce the expression of BBLe, BBLd-1, and/or BBLd-2 and/or reduce the activity of an additional berberine bridge enzyme-like polypeptide such as BBLe, BBLd-1, and/or BBLd-2.

In some embodiments, the invention further comprises reducing expression of a polynucleotide encoding a transcription factor that positively regulates nicotinic alkaloid biosynthesis in a *Nicotiana* plant or plant part. Thus, in some embodiments, the *Nicotiana* plant or plant part may be further modified to reduce expression of at least one polynucleotide encoding a transcription factor that positively regulates nicotinic alkaloid biosynthesis. Non-limiting examples of transcription factors that positively regulate nicotinic alkaloid biosynthesis include ERF family transcription factors such as ERF189, ERF221 and ERF32, and/or bHLH family transcription factors such as NtMYC1 and NMYC2, and COI1.

In some embodiments, a *Nicotiana* plant of the invention may be further modified to overexpress at least one polynucleotide encoding a transcription factor that negatively regulates nicotinic alkaloid biosynthesis. Non-limiting examples of transcription factors that negatively regulate nicotinic alkaloid biosynthesis includes JAZ.

As used herein, "overexpress," "overexpression," "overexpressed," (and grammatical variations thereof) refer to the production of a gene product in a transgenic *Nicotiana* plant or plant part that exceeds the level of production of the same gene product in a control *Nicotiana* plant or plant part, the transgenic *Nicotiana* plant or plant part being transformed with a recombinant nucleic acid construct that confers the increased production of the gene product, whereas the control *Nicotiana* plant or plant part is not transformed with said recombinant nucleic acid construct.

The expression of any of additional polynucleotides to be altered in a *Nicotiana* plant of this invention may be reduced by any means known for introducing a mutation including gene editing and/or via introduction into the *Nicotiana* plant an interfering RNA developed to target the nucleic acids encoding any one or more of the additional nicotinic alkaloid biosynthetic enzymes. As is well known in the art, "interfering RNA" is RNA capable of causing gene silencing. Interfering RNA, as used herein, includes any type of RNA molecule capable of down-regulating or silencing expression of a target nicotinic alkaloid biosynthetic nucleic acid, including but not limited to sense RNA, antisense RNA, short interfering RNA (siRNA), microRNA (miRNA), double-stranded RNA (dsRNA), hairpin RNA (RNA) and the like.

In some embodiments, a seed of a *Nicotiana* plant of the invention and *Nicotiana* plants produced from the seed are provided, wherein the seed comprises (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2, wherein the *Nicotiana* plant has a nicotinic alkaloid content that is reduced as compared to a plant that is modified per (A) only (e.g., not modified per (A) and (B)). In some embodiments, a seed of a *Nicotiana* plant of the invention and *Nicotiana* plants produced from the seed are provided, wherein the seed comprises (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, wherein the *Nicotiana* plant has a nicotinic alkaloid content that is reduced as compared to a plant that is modified per (A) only (e.g., not modified per (A) and (B)). In some embodiments, a seed of a *Nicotiana* plant of the invention and *Nicotiana* plants produced from the seed are provided, wherein the seed comprises (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 and a recessive allele of nic2, wherein the *Nicotiana* plant has a nicotinic alkaloid content that is reduced as compared to a plant that is modified per (A) only (e.g., not modified per (A) and (B)).

In some embodiments, the invention provides a progeny *Nicotiana* plant produced from the *Nicotiana* plants of the invention. In some embodiments, further provided is a crop comprising a plurality of *Nicotiana* plants of the invention planted together in an agricultural field.

Additional aspects of the invention include a harvested product produced from the *Nicotiana* plants or plant parts of the invention, as well as a processed product produced from said harvested product. A harvested product can be a whole plant or any plant part, wherein said harvested product comprises a recombinant nucleic acid molecule/construct of the invention. Thus, in some embodiments, non-limiting examples of a harvested product include a seed, a fruit, a flower or part thereof (e.g., an anther, a stigma, and the like), a leaf, a stem, and the like.

Any tobacco or tobacco product may be produced using the *Nicotiana* plants of the present invention. In some embodiments, the tobacco produced may include, but is not limited to, leaf tobacco, shredded tobacco, cut tobacco, ground tobacco, powder tobacco, tobacco extract, smokeless tobacco, moist or dry snuff, pipe tobacco, cigar tobacco, cigarillo tobacco, cigarette tobacco, and/or chewing tobacco. In some embodiments, a tobacco product made using the tobacco of the present invention can include but is not limited to, a cigarillo, a kretek cigarette, a non-ventilated recess filter cigarette, a vented recess filter cigarette, a cigar, snuff, a tobacco-containing gum, a tobacco-containing lozenge, and/or a chewing tobacco.

In some embodiments, the present invention provides a tobacco product, wherein the product can be a blended tobacco product. In some embodiments of the invention, the tobacco product of the present invention can be a reduced nicotine tobacco product. In still other embodiments, the tobacco product of the present invention can be a blended tobacco product with reduced nicotine content. Thus, the tobacco product of the present invention can be a blended reduced nicotine tobacco product.

In some embodiments, the invention provides a reduced-nicotinic alkaloid tobacco product produced from a *Nicotiana* plant of the invention or plant part thereof having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2, wherein the *Nicotiana* plant or plant part thereof has a nicotinic alkaloid content that is reduced as compared to a plant that is modified per (A) only (e.g., not modified per (A) and (B)).

The present invention further provides a method of producing a blended tobacco, comprising: a) providing a first tobacco; b) providing a second tobacco, wherein the second tobacco is produced from a *Nicotiana* plant of the invention having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2; and c) blending said first tobacco with said second tobacco so as to produce said blended tobacco. In some embodiments, the first and the second tobacco may be produced from a *Nicotiana* plant of the invention, wherein, in some embodiments, the first tobacco and second tobacco are from different *Nicotiana* plant varieties both having reduced nicotinic alkaloid content and comprising a mutation in A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1 or a recessive allele of nic1 and a recessive allele of nic2.

In other aspects of the present invention, a method is provided for producing a blended reduced nicotine tobacco, the method comprising: a) providing a first tobacco; b) providing a second tobacco, wherein the second tobacco is produced from a *Nicotiana* plant of the invention having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2; and c) blending said first tobacco with said second tobacco so as to produce said blended reduced nicotine tobacco. In some embodiments, first and the second tobacco may be produced from a *Nicotiana* plant of the invention, wherein, in some embodiments, the first tobacco and second tobacco are from different *Nicotiana* plant varieties both having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2. As an example, both flue-cured and air-cured tobaccos are components of the common American blend cigarette. Thus, in some embodiments of the invention, a low nicotinic alkaloid tobacco product may be produced by blending a low nicotine burley variety with a high nicotine flue-cured variety, each variety having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2, thereby reducing the overall nicotinic alkaloid (e.g., nicotine, anatabine, nornicotine, anabasine, and the like) content of the low alkaloid tobacco product.

As is well known in the art, a tobacco formulation for a tobacco product can incorporate other components in addition to tobacco which can alter the bitterness, sweetness, sourness or saltiness of the formulation; enhance the perceived dryness or moistness of the formulation; or the degree of tobacco taste exhibited by the formulation. Such other components may be salts (e.g., sodium chloride, potassium chloride, sodium citrate, potassium citrate, sodium acetate, potassium acetate, and the like); natural sweeteners (e.g., fructose, sucrose, glucose, maltose, mannose, galactose, lactose, and the like); artificial sweeteners (e.g., sucralose, saccharin, aspartame, acesulfame K, and the like), organic and inorganic fillers (e.g., grains, processed grains, puffed grains, maltodextrin, dextrose, calcium carbonate, calcium phosphate, corn starch, lactose, manitol, xylitol, sorbitol, finely divided cellulose, and the like); binders (e.g., povidone, sodium carboxymethylcellulose and other modified cellulosic types of binders, sodium alginate, xanthan gum, starch-based binders, gum arabic, lecithin, and the like); pH adjusters or buffering agents (e.g., metal hydroxides, preferably alkali metal hydroxides such as sodium hydroxide and potassium hydroxide, and other alkali metal buffers such as potassium carbonate, sodium carbonate, sodium bicarbonate, and the like); colorants (e.g., dyes and pigments, including caramel coloring and titanium dioxide, and the like); humectants (e.g. glycerin, propylene glycol, and the like); preservatives (e.g., potassium sorbate, and the like); syrups (e.g., honey, high fructose corn syrup, and the like); disintegration aids (e.g., microcrystalline cellulose, croscarmellose sodium, crospovidone, sodium starch glycolate, pregelatinized corn starch, and the like); antioxidants (e.g., ascorbic acid, grape seed extracts and oils, polyphenol-containing materials such as green tea extract and black tea extract, peanut endocarb, potato peel, and the like (See Santhosh et al., *Phytomedicine,* 122:16-220 (2005); incorporated herein by reference); and flavoring agents. Flavoring agents may be natural or synthetic, and include, but are not limited to, fresh, sweet, herbal, confectionary, floral, fruity or spice. Specific types of flavors include, but are not limited to, vanilla, coffee, chocolate, cream, mint, spearmint, menthol, peppermint, wintergreen, lavender, cardamon, nutmeg, cinnamon, clove, cascarilla, sandalwood, honey, jasmine, ginger, anise, sage, licorice, grape, lemon, orange, apple, peach, lime, cherry, and strawberry. (See Leffingwill et al., *Tobacco Flavoring for Smoking*

*Products*, R. J. Reynolds Tobacco Company (1972)). Flavorings also can include components that are considered moistening, cooling or smoothening agents, including, but not limited to, *eucalyptus*. These flavors may be provided alone or in a composite (e.g., spearmint and menthol, or orange and cinnamon). Representative types of components are also set forth in U.S. Pat. No. 5,387,416 to White et al. and PCT Application Publication No. WO 2005/041699 to Quinter et al., the relevant portions of each of which is incorporated herein by reference. Thus, in some embodiments, a tobacco product of the invention may comprise a flavoring component or a scent.

The amount of tobacco within the tobacco formulation may vary. In particular embodiments, the amount of tobacco within the tobacco formulation is at least about 25 percent to at least about 40 percent, on a dry weight basis (e.g., 25, 26, 27, 28, 29, 30, 31, 32, 33, 34, 35, 36, 37, 38, 39, 40% dry weight, and any value or range therein). The amounts of other components within the tobacco formulation preferably are in excess of about 25 percent to about 40 percent, on a dry weight basis.

In some embodiments of the present invention, methods are provided wherein the amount of nicotine in a human that uses tobacco is reduced, the method comprising providing to said human any of the tobacco products of the present invention.

In still other aspects of the present invention, a method is provided for reducing the nicotine consumption of a tobacco user, the method comprising: (a) providing said tobacco user a first tobacco product comprising tobacco produced from a *Nicotiana* plant of the invention having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2; and (b) providing said tobacco user a second tobacco product comprising tobacco produced from a *Nicotiana* plant of the invention having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2; wherein said second tobacco product comprises less nicotine than said first tobacco product.

In some aspects of the invention, a tobacco user can be provided with additional tobacco products comprising tobacco produced from a *Nicotiana* plant of the invention having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2; wherein said additional tobacco products comprise sequentially reduced amounts of nicotine, starting with a third product that comprises less nicotine than said first or second tobacco product.

In some embodiments of the present invention tobacco-use cessation kits are provided, wherein the tobacco-use cessation kits comprise a tobacco product selected from the tobacco products of any of the products of the present invention produced from a *Nicotiana* plant of the invention having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2.

In some embodiments, the present invention provides a kit comprising a first tobacco product that comprises nicotine and a second tobacco product that comprises an amount of nicotine less than the amount in the first tobacco product, wherein said first or second tobacco product comprises a tobacco product produced from a *Nicotiana* plant of the invention having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2.

In some aspects, the present invention provides a product produced from a *Nicotiana* plant of the invention having reduced nicotinic alkaloid content and comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2, wherein the product produced is selected from the group consisting of industrial enzymes, pharmaceuticals, cosmetic components, human and livestock feeds, food additives, and fermentation products.

The present invention further provides methods for improving/increasing the yield and quality of the *Nicotiana* plant of the invention having (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2. In some embodiments, a method for improving the yield of the *Nicotiana* plant of the invention comprises: (a) fertilizing seedlings at a stage of about 90% germination, the fertilizing is carried out through fertigation (e.g., drip irrigation), optionally the concentration of N in the fertilizer is about 200 ppm; (b) applying a plastic mulch treatment; e.g., a plastic mulch is added to cover the fertigation equipment (e.g., drip tape/tube); and (c) applying nitrogen at a rate of about 90-120 lbs/acre N total, to the seedlings at about 4 to 5 weeks after transplanting, at about 6 to 7 weeks after transplanting, and at about 8 to 9 weeks after transplanting, to provide increased yield and quality of the *Nicotiana* plant.

As used herein, a "substrate" in which a *Nicotiana* plant and/or plant part thereof (e.g., seeds) is growing/planted refers to any media for germinating seeds and/or planting/growing a *Nicotiana* plant and may include, but is not limited to, natural soil, synthetic soil, planting media, soilless media (e.g., peatmoss, perlite, vermiculite and the like) and/or any combination thereof.

"Increased yield" as used herein refers to increased biomass, increased leaf number, increased leaf area, and/or increased stalk girth that is observed for tobacco plants comprising (A) a modification that reduces the activity of BBLa, BBLb, and BBLc or reduces expression of a nucleic acid encoding BBLa, a nucleic acid encoding BBLb, and a nucleic acid encoding BBLc; and (B) a recessive allele of nic1, or a recessive allele of nic1 and a recessive allele of nic2 when grown under the modified conditions described herein as compared to the same plant grown under standard tobacco growing conditions (e.g., fertilizer applied on the ground and later added on the sides (e.g., laid-by) and water supplied separately (rain or external irrigation; plastic mulch is not part of the standard growing procedures nor is the use of fertigation by drip tape (water plus fertilizer).

In some embodiments, nitrogen may be applied to the substrate (pre- and/or post planting) using fertigation. As used herein, "fertigation" refers to a fertilizer application in which fertilizer is incorporated within the irrigation water by a drip system. Fertigation provides even distribution of fertilizer solution via irrigation.

In some embodiments, the substrate in which the *Nicotiana* plants are planted may be covered to reduce weed growth and water loss as well as to better control the temperature of the substrate (e.g., keep more constant and/or increase the soil temperature). In some embodiments, the cover may be a plastic mulch (e.g., a ground cover sheeting), including, but not limited to a plastic ground cover sheeting (e.g., white plastic sheeting, black plastic sheeting).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

Evaluation of K326 Flue-Cured Tobacco Isolines Containing Mutations in BBL-a, BBL-b, and BBL-c (BBL Mutations (a, b and c)

Evaluation of eight K326 homozygous BBL mutant lines and corresponding controls in six field environments indicated that that the addition of no single BBL gene mutation had a significant effect to lower nicotine accumulation (FIG. 1). Only genotypes with mutations in both BBL-a and BBL-b exhibited significant (P<0.05) reductions in nicotine as compared to K326. The K326 (220) and K326 (222) mutant lines accumulated 0.45 and 0.38% nicotine, respectively, as compared to 2.69% for K326. Progressive decreases in nicotine were observed as the number of recessive alleles at the nic1 and nic2 loci increased in the genetic background of NC95. Nicotine levels in the triple homozygous mutant line K326 (222) were not lower than that for LAFC53, the nic1/nic1 nic2/nic2 isoline of flue-cured tobacco cultivar NC95.

Some small significant (P<0.05) reductions were observed for percent anatabine in single mutant lines, but not for anabasine (FIG. 1). Extreme reductions in percent anatabine were measured for K326 (220) and K326 (222). More modest, but still significant, reductions were found for percent anabasine for these two genotypes. Similar to nicotine, progressive decreases in anatabine and anabasine accumulation were found with the addition of recessive alleles at the nic1 and nic2 loci in an NC95 genetic background. Significant (P<0.05) increases in percent nornicotine were observed for the double mutant genotypes K326 (220) and K326 (222) (FIG. 1). No significant changes in percent reducing sugars were found amongst the K326 isolines or amongst the NC95 isolines. Table 2 provides a summary of the genotypes evaluated for alkaloid accumulation and agronomic traits in this Example.

TABLE 2

Genotypes evaluated for alkaloid accumulation and agronomic traits

| Line Designation | BBL Genotype | Nic1 + Nic2 Genotype |
|---|---|---|
| K326 | BBL-a/BBL-a BBL-b/BBL-b BBL-c/BBL-c | Nic1/Nic1 Nic2/Nic2 |
| K326 (000) | BBL-a/BBL-a BBL-b/BBL-b BBL-c/BBL-c | Nic1/Nic1 Nic2/Nic2 |
| K326 (002) | BBL-a/BBL-a BBL-b/BBL-b bbl-c/bbl-c | Nic1/Nic1 Nic2/Nic2 |
| K326 (020) | BBL-a/BBL-a bbl-b/bbl-b BBL-c/BBL-c | Nic1/Nic1 Nic2/Nic2 |
| K326 (200) | bbl-a/bbl-a BBL-b/BBL-b BBL-c/BBL-c | Nic1/Nic1 Nic2/Nic2 |
| K326 (022) | BBL-a/BBL-a bbl-b/bbl-b bbl-c/bbl-c | Nic1/Nic1 Nic2/Nic2 |
| K326 (202) | bbl-a/bbl-a BBL-b/BBL-b bbl-c/bbl-c | Nic1/Nic1 Nic2/Nic2 |
| K326 (220) | bbl-a/bbl-a bbl-b/bbl-b BBL-c/BBL-c | Nic1/Nic1 Nic2/Nic2 |
| K326 (111) | BBL-a/bbl-a BBL-b/bbl-b BBL-c/bbl-c | Nic1/Nic1 Nic2/Nic2 |
| K326 (222) | bbl-a/bbl-a bbl-b/bbl-b bbl-c/bbl-c | Nic1/Nic1 Nic2/Nic2 |
| NC95 | BBL-a/BBL-a BBL-b/BBL-b BBL-c/BBL-c | Nic1/Nic1 Nic2/Nic2 |
| MAFC5 | BBL-a/BBL-a BBL-b/BBL-b BBL-c/BBL-c | Nic1/Nic1 nic2/nic2 |
| LMAFC34 | BBL-a/BBL-a BBL-b/BBL-b BBL-c/BBL-c | nic1/nic1 Nic2/Nic2 |
| LAFC53 | BBL-a/BBL-a BBL-b/BBL-b BBL-c/BBL-c | nic1/nic1 nic2/nic2 |

Example 2

Introgression of the Recessive Alleles at the Nic1 and Nic2 Loci into BBL Mutations (a, b and c) and Field Evaluation This invention is directed in part to determining whether combining induced BBL mutations with the naturally occurring recessive alleles at the Nic1 and Nic2 loci could further lower nicotine accumulation in tobacco. For this purpose, the recessive alleles at the Nic1 or Nic2 loci were introgressed into K326 (222) having a genetic background comprising induced mutations in the three most highly expressed BBL gene family members (BBL-a, BBL-b, and BBL-c). K326 (222) was initially hybridized with LAFC53 (nic1/nic1 nic2/nic2). $BC_2F_1$ progeny were subsequently developed after backcrosses to K326 (222) accompanied with selection for the homozygous mutant condition at the BBL-a, BBL-b, and BBL-c loci using the previously described KASP markers and selection for the recessive nic1 and nic2 alleles using SNP markers described by Adams et al (2016). bbl-a/bbl-a bbl-b/bbl-b bbl-c/bbl-c Nic1/nic1 Nic2/nic2 $BC_2F_1$ individuals were self-pollinated and triple homozygous bbl mutant $BC_2F_2$ were identified via genotyping that were either Nic1/Nic1 nic2/nic2, nic1/nic1 Nic2/Nic2, or nic1/nic1 nic2/nic2. Such $BC_2F_2$ plants were self-pollinated to produce $BC_2F_3$ families that were evaluated in comparison with K326, K326 (222), and LAFC53 for nicotine accumulation in a single 2019 field environment near Clayton, NC. Plants were managed according to standard flue-cured production practices for North Carolina. The experimental design was a completely randomized design with each genotype being represented by between 12 and 37 plants. The top two leaves of each plant were harvested 21 days after topping, air cured, and analyzed for alkaloid profiles as previously described.

Example 3

Figure 2:
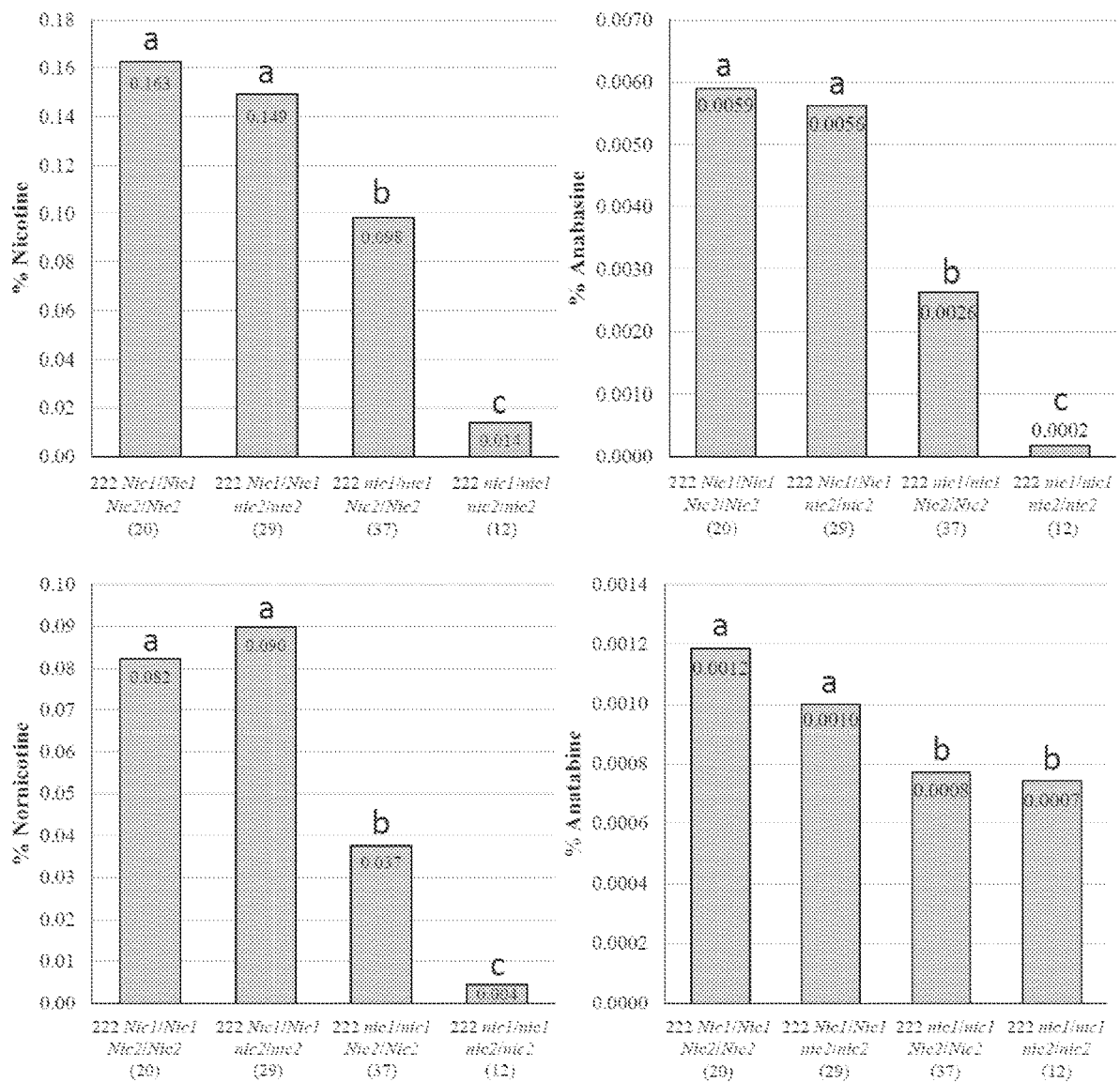
FIG. 2 shows mean alkaloid contents on a percent dry weight basis for top two leaves of $BC_2F_3$ individual plants fixed for mutations in BBL-a, BBL-b, and BBL-c, but segregating for recessive alleles at the Nic1 and Nic2 loci. Samples were collected 21 days after topping. Number of plants in each genotypic class is indicated within parentheses. Genotypic means are indicated on individual bars and means with the same letters are not significantly different from each other at the P>0.05 level of significance as determined by t-tests.

Alkaloid Analysis of the BBL Mutations (a, b and c) with Different Recessive Alleles at the Nic1 and Nic2 Loci As shown in FIG. 2, genotypes of the bbl-a/bbl-a bbl-b/bbl-b bbl-c/bbl-c genetic combination generally exhibited lower, but not significantly lower, alkaloid levels (with the exception of nornicotine) when combined with the recessive alleles at only the Nic2 locus in a K326 genetic background ("222 Nic1/Nic1 nic2/nic2"). Significant reductions in all alkaloids (P<0.05) were observed for bbl-a/bbl-a bbl-b/bbl-b bbl-c/bbl-c individuals also carrying the recessive alleles at only the Nic1 locus ("222 nic1/nic1 Nic2/Nic2") (FIG. 2). The lowest alkaloid levels were measured for bbl-a/bbl-a bbl-b/bbl-b bbl-c/bbl-c plants that were also homozygous for the recessive alleles at both the Nic1 and Nic2 loci ("222 nic1/nic1 nic2/nic2") (FIG. 2). The average nicotine content of plants with this genotype was very low (0.014%) (FIG. 2).

Example 4

Evaluation of Flue-Cured Tobacco Containing BBL Mutations (a, b and c) with Different Recessive Alleles at the Nic1 and Nic2 Loci Nicotiana plants of the present technology (K326 (222) nic1/nic1 nic2/nic2) were evaluated for yield, quality, and cured leaf chemistry in comparison with K326 (WT) and K326 (222) plants. Plants from four K326 (222) nic1/nic1 nic2/nic2 lines, two K326 (222) lines, along with K326 (WT) were grown in two rows of approximately 60-90 plants for each line with 3 replications, and managed according to standard flue-cured production practices for North Carolina. Value per hundred weight ($/Cwt) and value (S/A) were calculated based on a publicly available flue-cured tobacco price index. After harvesting and curing, alkaloid levels and cured leaf Grade Index values were measured. Oven-dried samples were ground to pass through a 1-mm sieve and analyzed for alkaloid profiles (expressed as a percentage of dry weight) as previously outlined by Lewis et al., PLOS ONE 10, e0117273 (2015).

As shown in Table 3, the Nicotiana plants of the present technology (K326 (222) nic1/nic1 nic2/nic2) having reduced nicotine levels maintained a yield and USDA Grade Index of cured leaf that is comparable to or improved as compared to wild-type control (K326) and Nic1/Nic2 controls (K326 (222)).

Example 5

Optimization of Field-Grown Tobacco Comprising BBL Mutations (a, b and c) with Different Recessive Alleles at the Nic1 and Nic2 Loci Tobacco Seedling Production Tobacco seedling production for the BBLabc/nic1-2 lines is performed similarly to wild type with the exception of some modifications. The greenhouse needs to be clean and free of weeds, decaying plant material, debris, algae, and any other items that may provide food or shelter for insects and other pests. Different float beds were used for seedlings of different ages and genetics. Ensure that at least a 1-foot buffer is maintained between float beds and is frequently renovated. Filling of float trays with standard seedling substrate/growing mix (e.g., Seedling Pro-Mix). When germination reaches 9010, flush the float bed water, and replace it with fresh water mixed with fertilizer (40-10-20) (N-P-K) with a nitrogen concentration of about 200) ppm. The first trimming should occur 2 or 3 weeks after fertilizer is added to the water and subsequent trimmings should be carried out periodically to ensure uniformity of the seedlings. The seedlings should be ready for transplanting when the stems have thickened up and they have grown at least about 3 inches above the soil line.

Cultivation and Harvest

Soil composition for seedling cultivation should be approximately 20% clay, 25% silt, and 55% sand. The drainage class should be moderate to well-drained, with a pH of about 6.5. Fertigation is used to apply half of the N as pre-plant with the other half split over three separate application periods at about four, six, and eight weeks after transplanting. A plastic mulch was added to cover the fertigation dripping tape or tube. The timing of fertigation is intended to capture three periods of N demand by the plant as follows. At four weeks after transplanting, the plant is "established" and entering a "rapid growth" stage, where about 80% of total biomass will be attained, and nitrogen will be in high demand by the plant. Two weeks later, the plant will be expected to be in the "rapid growth" stage. At week 8, after transplanting, the plant will be entering "flow-

TABLE 3

Entry means for flue-cured genetic materials evaluated for alkaloid levels, yield, and quality determinations

| Genotype | Yield (lbs/A) | Value ($/Cwt) | Value ($/A) | USDA Grade Index | Total Alkaloids (%) | Nicotine (%) | Nornicotine (%) | Anatabine (%) | Anabasine (%) |
|---|---|---|---|---|---|---|---|---|---|
| K326 (222) nic1/nic1 nic2/nic2 | 1870 | 156.69 | 2860.29 | 75.3 | 0.141 | 0.128 | 0.008 | 0.004 | 0.001 |
| K326 (222) nic1/nic1 nic2/nic2 | 2060 | 117.07 | 2465.80 | 59.9 | 0.172 | 0.149 | 0.016 | 0.005 | 0.002 |
| K326 (222) nic1/nic1 nic2/nic2 | 2070 | 158.11 | 3366.66 | 76.9 | 0.179 | 0.157 | 0.015 | 0.005 | 0.001 |
| K326 (222) nic1/nic1 nic2/nic2 | 2742 | 131.72 | 3665.62 | 66.2 | 0.191 | 0.177 | 0.009 | 0.005 | 0.001 |
| K326 (222) | 1691 | 121.92 | 2080.39 | 61.5 | 0.347 | 0.244 | 0.090 | 0.003 | 0.010 |
| K326 (222) | 1560 | 132.95 | 2038.10 | 65.4 | 0.364 | 0.254 | 0.096 | 0.004 | 0.009 |
| K326 (WT) | 2119 | 147.08 | 3084.23 | 72.9 | 2.806 | 2.655 | 0.072 | 0.065 | 0.014 |

Means are ranked in ascending order of % nicotine.
K326 (222) = bbl-a/bbl-a bbl-b/bbl-b bbl-c/bbl-c plants, also referred to as "K326abc"; K326 (222) nic1/nic1 nic2/nic2 = bbl-a/bbl-a bbl-b/bbl-b bbl-c/bbl-c plants that are also homozygous for the recessive alleles at both the Nic1 and Nic2 loci, i.e., bbl-a/bbl-a, bbl-b/bbl-b, bbl-c/bbl-c, nic1/nic1, nic2/nic2 ering" where water and N will be in demand to help the fully expanded leaves mature and attain high GRI quality.

The experiment was set up in a randomized complete block design, with three blocks, each containing different lines tested. The ground was turned, and pre-plant nitrogen applied at prescribed treatment amounts, then, was followed by sprayed herbicides and fungicides. The plastic mulch was applied between this spraying and the transplanting of the seedlings into the bed. Four to five weeks after transplanting, the plasticulture was fertigated. Another application was made 6-7 weeks later, and finally, the last application was 8-9 weeks after transplanting. At the flowering stage, plants were topped and sprayed with sucker control. The different lines were not harvested at the same time or in a conventional way due to the fact that the BBLabc/nic1-2 combinations matured at a different rate from the wild type control. Typically, wild type tobacco leaves are harvested when they are fully mature and ripe. Mature leaves exhibit a slight yellowing and puckering between veins and break off the stalk easier than immature leaves. In the BBLabc/nic1-2 combinations lines, this process is accelerated in the bottom leaves and is different from the upper leaf in comparison to wild type lines. The yellowing and texture of the leaf are different from a normal wild type. Harvest yield data was a measurement of the biomass achieved in the interior two sample rows projected into an acreage estimation.

Example 6

Optimization of Flue-Curing Process of BBL Mutations (a, b and c) with Different Recessive Alleles at the Nic1 and Nic2 Loci The kiln was filled (full and evenly packed) with freshly harvested leaves from one genetic background at a time. The leaf material placed in the kiln was of as similar a quality as possible. Analog thermometers and digital sensors were used to keep track of the Dry Bulb Temperature (DBT) and Wet Bulb Temperature (WBT). Leaves were monitored during the curing process. The initial parameters were the following and are based on Powell 1987 (Manual entitled Powell Manufacturing, Co.'s Bulk Curing/Drying Owner's Operator's Manual for Flue Cured Tobaccos, Powell Manufacturing, Co. (Jan. 20, 1987)) with some modifications. For instance, the upper temperature limit was increased to 104-108° F., and the lower temperature limit was decreased to 92-96° F., with a rate of increase 1° F. per hour until reaching maximum upper temperature and holding at the upper temperature for a period of about 52-58 hours. The yellowing step in curing is typically 48 hours; however, here this step was extended to 52-58 hours with continuous monitoring of the temperature and the leaf color. The modification in length of time and temperature is due to the higher content of chlorophyll (leaf greenness) resulting from the introduction of the recessive alleles of Nic1 and/or Nic2. Once the majority of each leaf has turned yellow, and most of the green color is restricted to the veins of the leaf, the yellowing phase is ended.

The next step is the "leaf drying" phase. This phase is typically about 24 hours, but here was reduced to 22 hours. For the leaf drying, the upper limit temperature (ULT) was raised to 120° F. After this step, the leaves were orange/red color. The last phase of curing is stem drying. Stem drying was initiated by raising the ULT to 135° F., resulting in the complete drying of the leaves (18% humidity).

When cultivated and cured by the methods of the present technology, the cured tobacco leaf (including leaf, smoking leaf, tips, cutter, lugs) of the present technology has the characteristics of good to fair quality leaf with good color intensity, normal width and uniform texture, in comparison to a standard procedure of tobacco growing (including rain fed) and curing that produces a poor to low quality leaf with this *Nicotiana* plant. For example, the BBLabc nic1-2 strains cultivated and cured by the methods of the present technology produced a fair quality orange for the smoking leaf (H4F), a fair quality lemon cutters (C4L), and a fair quality orange (P4F) for the priming leaf. In some embodiments, in general the cured tobacco leaf of this invention may have a USDA grade index of over 60. Accordingly, the cultivation and curing methods of the present technology are useful for producing a cured tobacco leaf of commercial quality having ultra-low nicotine levels.

Example 7

Optimization of Field-Grown Tobacco Plants Comprising BBL Mutations (a, b and c) with Different Recessive Alleles at the Nic1 and Nic2 Loci The ultra-low nicotine levels of 0.04% recommended by the World Health Organization are not routinely observed amongst the lowest-alkaloid tobacco available today. To date, the only known tobacco line that has achieved an ultra-low nicotine level below 0.04% is Vector 21-41 GMO variety. This variety was developed using antisense RNA to specifically suppress expression of a gene encoding quinolate phosporibosyltransferase, an enzyme involved in nicotine biosynthesis in tobacco roots (Xie et al., 2004), under a genetic background of the recessive alleles at the Nic1 and Nic2 loci (also known as A and B). These loci have been found to contribute to major reductions in nicotine and associated alkaloids (e.g., nornicotine, anabasine, and anatabine) from between 1.5 and 4.5% to approximately 0.20 to 0.45% (Legg et al. *Can. J. Genet Cytol.* 13:287-291 (1971); Lewis, *Nicotine & Tobacco Res*. Pages 1-5 (2018) doi: 10109/ntr/nty022).

Seminal work by Chaplin and Weeks (Crop Sci. 16:416-418 (1976)), where they introgressed the recessive alleles of Nic1 and Nic2 into ten different tobacco genetic backgrounds, indicated that seven out of ten lines showed a reduction of yield. Furthermore, three lines did not show any reduction in nicotine compared to recurrent parent. The USDA grade index was lower for three out of seven of the lines due to the darker color of the cured leaf for the seven low alkaloid lines of the cured leaf compared to the recurrent parent. Three of the nic1 and nic2 introgressed lines exhibited a grade index equal to or better than the parent. It may be that there is a genetic background component that might help mitigate the effect of the nic1 and nic2 recessive alleles in those lines. In addition, most of the nic1 and nic2 introgressed lines exhibited a reduction of sugar (7-28%) and nitrogen content (10-25%) in comparison to recurrent parent. A general characteristic is that leaves were greener in appearance in comparison to the parent and likely contained a higher content of chlorophyll. In addition, it was observed that the ripening of the leaves was not normal (i.e., not the same as the recurrent parent plant).

These same characteristics were observed in the combination of the nic1 and nic2 recessive alleles introgressed into tobacco plant comprising the BBL mutations (a, b and c) but with a milder expression. Lines containing BBL mutations (a, b and c) provide a lower yield (10-30%) depending on the growth conditions and a lower grade index (9-16%) (Lewis et al., PLOS ONE 10:e0117273 (2015)); however, the chlorophyll content and sugar content is not affected. Tobacco plants comprising BBL mutations (a, b and c) in combination with the recessive Nic1 and Nic2 alleles (individually or together) provide lower nicotine levels but this combination may negatively affect the yield and leaf grade index of the tobacco plants. The methods and modifications of the present technology for growing and curing of the tobacco lines comprising the BBLabc mutations combined with the recessive Nic1 and Nic2 alleles (individually or together) aim to mitigate issues such as reduced nitrogen content, reduced sugar content and high chlorophyll content that may negatively impact the yield and quality of the leaf produced by these lines. Thus, the tobacco cultivation and curing protocols of the present technology that may be useful with the tobacco lines of this invention (e.g., BBLabc plus nic1; BBLabc plus nic1 and nic2) are as follows:

(a) At the stage of about 90% seedling germination, the float bed water is flushed and replaced with fresh water mixed with fertilizer (40-10-20) (N-P-K). The amount of nitrogen is higher than under standard growing conditions at about 200 ppm. Seedlings should be transferred when their height reaches at least about 3 inches above the soil line.

(b) Fertigation is used to apply about half of the N as pre-plant (e.g., via a drip tape) with the other half split over three separate application in particular periods of the plant growth at four-five, six-seven, and eight-nine weeks after transplanting (see page 43, last paragraph). Fertilizing is done primarily through drip irrigation at a rate of about 90-120 lbs/acre N total.

(c) To help to raise temperature and improve the seedling growth, plastic mulch is used to cover raised beds.

(d) The ripening process of the leaf in the BBLabc/nic1-2 lines is not typical for tobacco. In this case, the process is accelerated in the bottom leaves and is different from the upper leaf in comparison to the wild type lines. Extra nitrogen is applied before topping (at a rate of about 90-120 lbs per acre). The yellowing and texture of the leaf are different from a typical wild type tobacco leaf. Leaves should be harvested when they are green-yellow color.

(e) It was determined that, for curing, a wider temperature range and a longer yellowing process were needed. Thus, the upper temperature limit was increased to 108° F., and the lower temperature limit was decreased to 92° F., with a rate of increase 1° F. per hour from the lower to the upper temperature limit. The yellowing step in curing is usually 48 hours; however, here this step was extended to 52-58 hours (or more depending on the yellowing) with continuous monitoring of temperature and leaf color.

Example 8

Tobacco Leaves from Plants Comprising BBL (a, b and c) Mutations with Different Recessive Alleles at the Nic1 and Nic2 Loci that are Cultivated and Cured According to the Methods of the Present Technology are Characterized by Improved Quality as Compared to Tobacco Leaves from Plants Cultivated and Cured According to Standard Methods Control tobacco plants (K326 (WT)) and K326 (222) tobacco plants comprising BBL a, b, and c mutations (bbl-a bbl-a, bbl-b bbl-b, bbl-c bbl-c) and K326 (222) nic1/nic1 nic2/nic2 tobacco plants comprising BBL a, b, and c mutations (bbl-a bbl-a, bbl-b bbl-b, bbl-c bbl-c) that are also homozygous for the recessive alleles at both the Nic1 and Nic2 loci (nic1/nic1, nic2/nic2) prepared according to Example 2 were cultivated and cured according to either a standard process known in the art such as Powell 1987 (Manual entitled Powell Manufacturing, Co.'s Bulk Curing/Drying Owner's Operator's Manual for Flue Cured Tobaccos, Powell Manufacturing, Co. (Jan. 20, 1987) ("Standard NC") or the method of present technology ("New-H") as described in Examples 5-7.

Two field trials were performed. The tobacco plants from both the "Standard NC" and "New-H" groups were grown in the same field. Leaves were harvested from several lines (>10) for each of the individual genetic backgrounds. Various tobacco quality parameters were measured by sending 100 gram samples of cured leaf to laboratories (Global Lab Services and Enthalpy Analytical) for chemistry evaluation.

Results

As shown in Table 4, several parameters indicative of tobacco leaf quality were measured in leaves harvested from control and K326 (222) and K326 (222) nic1/nic1 tobacco plants that were cultivated and cured according to either standard methods or the methods of the present technology.

TABLE 4

Quality of cured tobacco leaves

| Cultivation/ Curing Process* | Control and Test Lines | Ammonia (%) | Nicotine (mg/g) | Nornicotine (ppm) | Reducing Sugar (% DWB) | Total sugar (% as is) | Moisture (%) |
|---|---|---|---|---|---|---|---|
| Standard NC | K326 (WT) | 0.076 | 14 | 341 | 10.6 | 10.5 | 10.1 |
| Standard NC | K326 (222) | 0.016 | 2.07 | 100 | 3.5 | 3.7 | 10.5 |
| Standard NC | K326 (222) nic1/nic1 nic2/nic2 | 0.067 | 0.28 | 138 | 3.4 | 3.5 | 11.2 |
| New-H | K326 (WT) | 0.02 | 17 | 403 | 3.7 | 5.03 | 14.30 |
| New-H | K326 (222) | 0.01 | 2.3 | 322 | 18.1 | 18.3 | 8 |
| New-H | K326 (222) nic1/nic1 nic2/nic2 | 0.04 | 0.37 | 674 | 14.2 | 13.6 | 9 |

*Results based on field trial experiments (Data was obtained form GLS and Enthalpy A.)

Control = K326 (WT); Test Lines = K326 (222) bbl-a/bbl-a bbl-b/bbl-b bbl-c/bbl-c plants, also referred to as "K326abc"; K326 (222) nic1/nic1 nic2/nic2 = bbl-aibbl-a bbl-b/bbl-b bbl-c/bbl-c plants that are also homozygous for the recessive alleles at both the Nic1 and Nic2 loci, i.e., bbl-a/bbl-a, bbl-b/bbl-b, bbl-c/bbl-c, nic1/nic1, nic2/nic2; DWB = dry weight basis Overall, the leaves from K326 (222) and K326 (222) nic1/nic1 nic2/nic2 tobacco plants grown and cured according to the methods of the present technology had a better grade, texture, color, and high-good quality as compared to leaves from plants grown and cured according to the standard method. As demonstrated by the results shown in Table 4, leaves from K326 (222) and K326 (222) nic1/nic1 nic2/nic2 tobacco plants grown and cured according to the methods of the present technology (i.e., K326 (222) and K326 (222) nic1/nic1 nic2/nic2 cultivated and cured according to the "New-H" method) contained more sugar as compared to the leaves from plants cultivated and cured according to standard methods (i.e., K326 (222) and K326 (222) nic1/nic1 nic2/nic2 tobacco plants cultivated and cured according to the "Standard NC" method). The sugar level in a flue-cured variety is a good indicator of a good flavor bright leaf. In addition, leaves from K326 (222) and K326 (222) nic1/nic1 nic2/nic2 lines grown and cured according to the methods of the present technology were characterized by a reduced percentage of ammonia as compared to leaves from K326 (222) and K326 (222) nic1/nic1 nic2/nic2 lines grown and cured according to standard methods. Ammonia percentage is typically used as an indicator of off-taste in tobacco. Similar results were obtained with total nitrogen (data not shown). Evaluation of acetaldehyde and formaldehyde did not show significant differences (data not shown).

Accordingly, these results demonstrate that the cultivation and curing methods of the present technology are useful for producing a cured tobacco leaf having improved quality and very low nicotine levels.

The foregoing is illustrative of the invention, and is not to be construed as limiting thereof. The invention is defined by the following claims, with equivalents of the claims to be included therein.

That which is claimed is:

1. A method of curing one or more leaves of a *Nicotiana* plant comprising:
   (A) a modification that reduces the activity of BBLa, BBLb, and BBLc or reduces expression of a nucleic acid encoding BBLa, a nucleic acid encoding BBLb, and a nucleic acid encoding BBLc; and
   (B) a homozygous recessive allele of nic1 or a homozygous recessive allele of nic1 and a homozygous recessive allele of nic2,
   the method comprising:
   (a) a yellowing process comprising heating the leaf at a temperature starting at 92° F.-96° F. and increasing to a temperature of 104° F.-108° F. at a rate of about 1° F. per hour until reaching a maximum upper temperature and holding at the upper temperature for a period of about 52-58 hours;
   (b) a leaf drying process comprising drying at a temperature of about 120° F. for about 22 hours; and
   (c) a stem drying process comprising drying at a temperature of about 132° F.-138° F. for about 50 hours to about 65 hours,
   thereby curing the one or more leaves of the *Nicotiana* plant and producing one or more cured leaves of the *Nicotiana* plant.

2. The method of claim 1, wherein the *Nicotiana* plant comprises (A) a modification that reduces the activity of BBLa, BBLb, and BBLc or reduces expression of a nucleic acid encoding BBLa, a nucleic acid encoding BBLb, and a nucleic acid encoding BBLc; and (B) a homozygous recessive allele of nic 1 and a homozygous recessive allele of nic2.

3. The method of claim 1, wherein the *Nicotiana* plant has a nicotinic alkaloid content that is reduced as compared to a modified *Nicotiana* plant comprising a modification that reduces the activity of BBLa, BBLb, and BBLc or reduces expression of a nucleic acid encoding BBLa, a nucleic acid encoding BBLb, and a nucleic acid encoding BBLc.

4. A cured leaf of the *Nicotiana* plant produced by the method of claim 1, wherein the cured leaf comprises (A) a modification that reduces the activity of BBLa, BBLb, and BBLc or reduces expression of a nucleic acid encoding BBLa, a nucleic acid encoding BBLb, and a nucleic acid encoding BBLc; and (B) a homozygous recessive allele of nic1 or a homozygous recessive allele of nic1 and a homozygous recessive allele of nic2.

5. The cured leaf of claim 4, wherein the leaf comprises a reduced nicotinic alkaloid content as compared to a leaf of a wild-type control *Nicotiana* plant or as compared to a Nic1/Nic2 control *Nicotiana* plant.

6. The cured leaf of claim 5, wherein:
   (a) the nicotinic alkaloid is nicotine; and/or
   (b) the leaf comprises a nicotine content of about 0.5 mg/g or less; and/or
   (c) the leaf comprises a nicotine content of about 0.4 mg/g or less.

7. The cured leaf of claim 4, wherein the leaf comprises increased levels of sugar and/or reduced levels of ammonia as compared to a leaf that was cured according to standard curing methods.

8. The cured leaf of claim 4, wherein the *Nicotiana* plant further comprises reduced expression of a polynucleotide encoding an additional nicotinic alkaloid biosynthetic enzyme selected from the group consisting of aspartate oxidase, quinolinate synthase, quinolate phosphoribosyl transferase, ornithine decarboxylase, putrescine N-methyl-transferase, methyl putrescine oxidase, and A622.

9. A tobacco product comprising the cured leaf of claim 4,
   wherein the tobacco is selected from the group consisting of leaf tobacco, shredded tobacco, cut tobacco, ground tobacco, powder tobacco, tobacco extract, smokeless tobacco, moist or dry snuff, pipe tobacco, cigar tobacco, cigarillo tobacco, cigarette tobacco, and chewing tobacco, and/or
   wherein the product is selected from the group consisting of a cigarillo, a kretek cigarette, a non-ventilated recess filter cigarette, a vented recess filter cigarette, a cigar, snuff, a tobacco-containing gum, a tobacco-containing lozenge, and a chewing tobacco.

* * * * *

UNITED STATES PATENT AND TRADEMARK OFFICE
CERTIFICATE OF CORRECTION

PATENT NO. : 12,171,177 B2  
APPLICATION NO. : 17/785153  
DATED : December 24, 2024  
INVENTOR(S) : Lewis et al.

Page 1 of 1

It is certified that error appears in the above-identified patent and that said Letters Patent is hereby corrected as shown below:

In the Specification

Column 24, Line 33: Please correct "$0.0^{98}\%$." to read --0.098%.--

Column 26, Line 43: Please correct "118°" to read --138°--

Column 26, Line 45: Please correct "59, 6, 61," to read --59, 60, 61,--

Column 47, Line 10: Please correct "Keinanen" to read --Keinänen--

Column 47, Line 53: Please correct "NMYC2" to read --NtMYC2--

Column 53, Line 43: Please correct "c)" to read --c))--

Column 55, Line 26: Please correct "(S/A)" to read --($/A)--

Column 56, Line 18: Please correct "9010" to read --90%--

Column 56, Line 20: Please correct "200) ppm." to read --200 ppm.--

Signed and Sealed this  
Eighth Day of July, 2025

Coke Morgan Stewart  
*Acting Director of the United States Patent and Trademark Office*